US011674889B2

(12) United States Patent
Kato et al.

(10) Patent No.: US 11,674,889 B2
(45) Date of Patent: Jun. 13, 2023

(54) CULTURE STATE DETERMINATION BASED ON DIRECTION-DEPENDENT IMAGE INFORMATION

(71) Applicant: Panasonic Intellectual Property Management Co., Ltd., Osaka (JP)

(72) Inventors: Yumiko Kato, Osaka (JP); Yoshihide Sawada, Tokyo (JP); Taichi Sato, Kyoto (JP); Kiyotaka Tsuji, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 466 days.

(21) Appl. No.: 16/842,902

(22) Filed: Apr. 8, 2020

(65) Prior Publication Data
US 2020/0232967 A1 Jul. 23, 2020

Related U.S. Application Data

(63) Continuation of application No. PCT/JP2018/036788, filed on Oct. 2, 2018.

(30) Foreign Application Priority Data

Nov. 28, 2017 (JP) .............................. JP2017-228021

(51) Int. Cl.
*G01N 33/483* (2006.01)
*G01N 21/17* (2006.01)
(Continued)

(52) U.S. Cl.
CPC .......... *G01N 21/17* (2013.01); *G06T 7/0012* (2013.01); *G06T 7/11* (2017.01); *G06T 7/557* (2017.01);
(Continued)

(58) Field of Classification Search
None
See application file for complete search history.

(56) References Cited

U.S. PATENT DOCUMENTS 9,865,054 B2    1/2018  Tsumura
10,401,276 B2   9/2019  Hayashi et al.
(Continued)

FOREIGN PATENT DOCUMENTS

JP        2009-044974        3/2009
WO   WO-2006100562 A2 *    9/2006   ......... G01N 33/5011
(Continued)

OTHER PUBLICATIONS

International Search Report of PCT application No. PCT/JP2018/036788 dated Dec. 18, 2018.
(Continued)

*Primary Examiner* — Patrick F Valdez
(74) *Attorney, Agent, or Firm* — McDermott Will & Emery LLP

(57) ABSTRACT

The present disclosure provides a technique which makes it possible to evaluate a state of a cell aggregation of one or more spheroids. In the culture state determination device according to the present disclosure, a plurality of light sources sequentially illuminate a plurality of cell aggregations put on an image sensor. The image sensor acquires captured images of the plurality of the cell aggregations each time when the plurality of the light sources illuminate the plurality of the cell aggregations. Control circuitry extracts a region including an image of the cell aggregation in the captured image; generates three-dimensional image information of the region using a plurality of the captured images; extracts an outer shape of the cell aggregation and a cavity part inside the cell aggregation using the three-dimensional image information; calculates a first volume that is a volume based on the outer shape of each of the cell aggregation and
(Continued)

a second volume that is a volume of the cavity part based on the cavity part of each of the cell aggregation in the three-dimensional image information; and determines a culture state of the cell aggregations using the first volume and the second volume.

4 Claims, 22 Drawing Sheets

(51) Int. Cl.
| | | |
|---|---|---|
| *G06T 7/62* | (2017.01) | |
| *G06T 7/11* | (2017.01) | |
| *G06T 7/557* | (2017.01) | |
| *G06T 7/00* | (2017.01) | |
| *G06T 15/00* | (2011.01) | |

(52) U.S. Cl.
CPC ............... *G06T 7/62* (2017.01); *G06T 15/00* (2013.01); *G01N 33/4836* (2013.01); *G06T 2207/10056* (2013.01); *G06T 2207/30024* (2013.01)

(56) References Cited

U.S. PATENT DOCUMENTS

| | | | |
|---|---|---|---|
| 2012/0142095 A1* | 6/2012 | Yano | C12M 41/14 |
| | | | 435/325 |
| 2014/0320513 A1* | 10/2014 | Ogi | G06V 20/695 |
| | | | 345/581 |
| 2015/0309301 A1* | 10/2015 | Motomura | G02B 21/0008 |
| | | | 348/79 |
| 2017/0192219 A1* | 7/2017 | Kato | G02B 21/18 |
| 2017/0257538 A1* | 9/2017 | Kokubo | G02B 21/0032 |
| 2017/0269344 A1 | 9/2017 | Kato et al. | |
| 2017/0358081 A1* | 12/2017 | Tsumura | G01N 21/253 |
| 2019/0244349 A1* | 8/2019 | Senda | C12M 1/34 |

FOREIGN PATENT DOCUMENTS

| | | |
|---|---|---|
| WO | 2015/145872 | 10/2015 |
| WO | 2016/117089 | 7/2016 |
| WO | 2016/158719 | 10/2016 |

OTHER PUBLICATIONS

"Cell3iMager Estier", Catalog provided by SCREEN holdings Co., Ltd., Published in Oct. 2017.

* cited by examiner

FIG. 4

| IMAGE FILE ID | ILLUMINATION POSITION |
|---|---|
| ⋮ | |
| $n$ | ( $x_n$, $y_n$, $za$ ) |
| $n+1$ | ( $x_{n+1}$, $y_{n+1}$, $za$ ) |
| $n+2$ | ( $x_{n+2}$, $y_{n+2}$, $za$ ) |
| ⋮ | |

FIG. 5

| REGION ID | COORDINATES OF REGION | |
|---|---|---|
| ⋮ | | |
| $A_m$ | ( $Ixa_m$, $Iya_m$ ) | ( $Ixb_m$, $Iyb_m$ ) |
| $A_{m+1}$ | ( $Ixa_{m+1}$, $Iya_{m+1}$ ) | ( $Ixb_{m+1}$, $Iyb_{m+1}$ ) |
| $A_{m+2}$ | ( $Ixa_{m+2}$, $Iya_{m+2}$ ) | ( $Ixb_{m+2}$, $Iyb_{m+2}$ ) |
| ⋮ | | |

| FOCAL PLANE ID | DISTANCE FROM SURFACE OF IMAGE SENSOR |
|---|---|
| FP1 | 1 μm |
| FP2 | 2 μm |
| FP3 | 3 μm |
| ⋮ | ⋮ |
| FP199 | 199 μm |
| FP200 | 200 μm |

FIG. 8

| REGION ID | COORDINATES OF REGION | DISTANCE FROM SURFACE OF IMAGE SENSOR | FOCAL PLANE IMAGE ID |
|---|---|---|---|
| ⋮ | ⋮ | ⋮ | ⋮ |
| $A_m$ | $(Ixa_m, Iya_m)$ | 1 μm | $IA_mF_1$ |
| | $(Ixb_m, Iyb_m)$ | 2 μm | $IA_mF_2$ |
| | | 3 μm | $IA_mF_3$ |
| | | ⋮ | ⋮ |
| | | 199 μm | $IA_mF_{199}$ |
| | | 200 μm | $IA_mF_{200}$ |
| $A_{m+1}$ | $(Ixa_{m+1}, Iya_{m+1})$ | 1 μm | $IA_{m+1}F_1$ |
| | $(Ixb_{m+1}, Iyb_{m+1})$ | 2 μm | $IA_{m+1}F_2$ |
| | | 3 μm | $IA_{m+1}F_3$ |
| | | ⋮ | ⋮ |
| | | 199 μm | $IA_{m+1}F_{199}$ |
| | | 200 μm | $IA_{m+1}F_{200}$ |
| $A_{m+2}$ | $(Ixa_{m+2}, Iya_{m+2})$ | 1 μm | $IA_{m+2}F_1$ |
| | $(Ixb_{m+2}, Iyb_{m+2})$ | 2 μm | $IA_{m+2}F_2$ |
| | | 3 μm | $IA_{m+2}F_3$ |
| | | ⋮ | ⋮ |

FIG. 9C
IMAGE OF FOCAL PLANE Fc
FOCUSED IMAGE
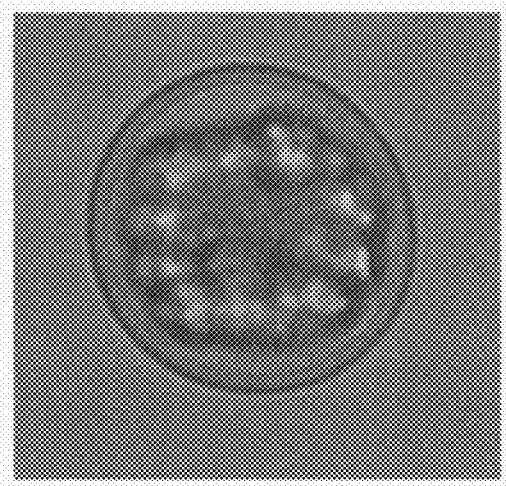
BINARIZED IMAGE
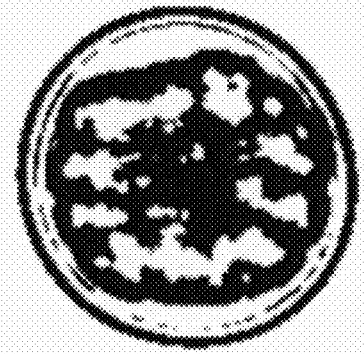
EXTRACTED IMAGE
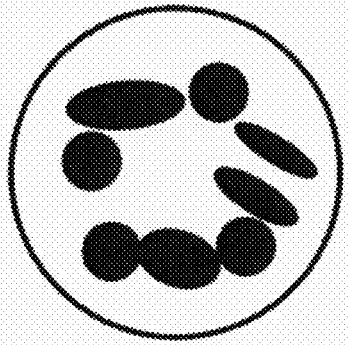

FIG. 10

| REGION ID | FOCAL PLANE IMAGE ID | DISTANCE FROM SURFACE OF IMAGE SENSOR | NUMBER OF PIXELS IN SPHEROID (FIRST PIXELS) | NUMBER OF PIXELS IN CAVITY PART (SECOND PIXELS) |
|---|---|---|---|---|
| ⋮ | ⋮ | ⋮ | ⋮ | ⋮ |
| $A_m$ | $IA_mF_1$ | 1 μm | $A_mPs_1$ | $A_mPc_1$ |
| | $IA_mF_2$ | 2 μm | $A_mPs_2$ | $A_mPc_2$ |
| | $IA_mF_3$ | 3 μm | $A_mPs_3$ | $A_mPc_3$ |
| | ⋮ | ⋮ | ⋮ | ⋮ |
| | $IA_mF_{199}$ | 199 μm | $A_mPs_{199}$ | $A_mPc_{199}$ |
| | $IA_mF_{200}$ | 200 μm | $A_mPs_{200}$ | $A_mPc_{200}$ |
| $A_{m+1}$ | $IA_{m+1}F_1$ | 1 μm | $A_{m+1}Ps_1$ | $A_{m+1}Pc_1$ |
| | $IA_{m+1}F_2$ | 2 μm | $A_{m+1}Ps_2$ | $A_{m+1}Pc_2$ |
| | $IA_{m+1}F_3$ | 3 μm | $A_{m+1}Ps_3$ | $A_{m+1}Pc_3$ |
| | ⋮ | ⋮ | ⋮ | ⋮ |
| | $IA_{m+1}F_{199}$ | 199 μm | $A_{m+1}Ps_{199}$ | $A_{m+1}Pc_{199}$ |
| | $IA_{m+1}F_{200}$ | 200 μm | $A_{m+1}Ps_{200}$ | $A_{m+1}Pc_{200}$ |
| $A_{m+2}$ | $IA_{m+2}F_1$ | 1 μm | $A_{m+2}Ps_1$ | $A_{m+2}Pc_1$ |
| | $IA_{m+2}F_2$ | 2 μm | $A_{m+2}Ps_2$ | $A_{m+2}Pc_2$ |
| | $IA_{m+2}F_3$ | 3 μm | $A_{m+2}Ps_3$ | $A_{m+2}Pc_3$ |
| | ⋮ | ⋮ | ⋮ | ⋮ |

FIG. 23

| PIXEL POSITION (COORDINATES) | LABEL (REGION ID) |
|---|---|
| ( 4 , 4 ) | 001 |
| ( 4 , 5 ) | 001 |
| ( 4 , 6 ) | 001 |
| ( 5 , 4 ) | 001 |
| ( 5 , 5 ) | 001 |
| ( 6 , 4 ) | 001 |
| ( 4 , 9 ) | 002 |
| ( 4 , 10 ) | 002 |
| ( 5 , 8 ) | 002 |
| ( 5 , 9 ) | 002 |
| ( 6 , 8 ) | 002 |
| ( 8 , 6 ) | 003 |
| ( 9 , 6 ) | 003 |
| ( 10 , 5 ) | 003 |
| ( 10 , 6 ) | 003 |
| ( 11 , 6 ) | 003 |
| ( 11 , 7 ) | 003 |
| ( 12 , 7 ) | 003 |
| ⋮ | ⋮ |

CULTURE STATE DETERMINATION BASED ON DIRECTION-DEPENDENT IMAGE INFORMATION

BACKGROUND

1. Technical Field

The present disclosure relates to a culture state determination utilizing a technique for generating an image of an object at an arbitrary focal plane.

2. Description of the Related Art

Continuous observation of cultured cells without staining is required in many fields where the cultured cells are used in medical and industrial fields, such as production of therapeutic cells and testing of drug efficacy. As a culture method, there is a method of culturing cells as a cell aggregation referred to as a spheroid. In order to determine quality of a state of a spheroid containing a large number of cultured cells, a technique for determining the state of the cultured cells based on a captured image of the spheroid using a microscope has been proposed.

For example, Patent Literatures 1 to 3 disclose techniques for determining the quality of the state of the spheroid. In Patent Literature 1, an image of the spheroid is captured through a microscope, and the circularity and sharpness of the outer shape of the spheroid are determined from the acquired image, and the collapse state of the spheroid is determined from the luminance distribution of the spheroid image. In addition, in Patent Literature 2, the quality of the state of the spheroid is determined from the circularity of the outline of the spheroid in the image. In addition, in Patent Literature 3, by manipulating the gene of the cell contained in the spheroid, the cell is adjusted in such a way that a photoprotein is produced, and emits light without a light source. Furthermore, the three-dimensional information of the spheroid is synthesized from the result of the image provided by capturing the spheroid including the above-described cells at the plurality of the focal planes using the microscope.

CITATION LIST

Patent Literature

Patent Literature 1: WO2015/145872
Patent Literature 2: WO2016/158719
Patent Literature 3: WO2016/117089
Patent Literature 4: United States Patent Application Publication No. 2017/0192219

SUMMARY

However, since the techniques of Patent Literatures 1 and 2 evaluate the state of the spheroid from the shape of the spheroid and the luminance distribution on the surface of the spheroid, it is difficult to evaluate the state of the inside of the spheroid. Although the technique of Patent Literature 3 can evaluate the state the inside of the spheroid based on the three-dimensional information of the spheroid, since it manipulates the gene of the cell contained in the spheroid, it is difficult to use the technique for a cell for treatment. In addition, the techniques of Patent Literatures 1 to 3 can determine the quality of the culture state of individual spheroids; however, it is difficult to choose spheroids which are in a good culture state and usable from a large amount of spheroids cultured for medical use or industrial use.

The present disclosure provides a culture state determination device and a culture state determination method, both of which can evaluate the state of a cell aggregation such as one or more spheroids.

The culture state determination device of the present disclosure comprises:
a plurality of light sources;
an image sensor on which a cell aggregation is to be mounted; and
control circuitry which, in operation,
(a) repeatedly causes the image sensor to acquire a captured image including the cell aggregation when the cell aggregation is illuminated with each of the plurality of the light sources sequentially, to acquire a plurality of captured images;
wherein
each of the plurality of the captured images includes the cell aggregation,
(b) extracts an image region including the cell aggregation from each of the plurality of the captured images;
(c) generates three-dimensional image information with regard to the image region with the plurality of the captured images;
(d) calculates a first volume and a second volume from the three-dimensional image information;
wherein
the first volume is an entire volume of the cell aggregation; and
the second volume is a volume of a cavity part of the cell aggregation; and
(e) determines a culture state of the cell aggregation using the first volume and the second volume.

Another culture state determination device of the present disclosure comprises:
a plurality of light sources;
an image sensor on which a plurality of cell aggregations are to be mounted; and
control circuitry which, in operation,
(a) repeatedly causes the image sensor to acquire a captured image including at least one cell aggregation included in the plurality of the cell aggregations when the plurality of the cell aggregations are illuminated with each of the plurality of the light sources sequentially, to acquire a plurality of captured images;
wherein
each of the plurality of the captured images includes the at least one cell aggregation included in the plurality of the cell aggregations,
(b) extracts an image region including one cell aggregation from each of the plurality of the captured images;
(c) generates three-dimensional image information with regard to the image region with the plurality of the captured images;
(d) calculates a first volume and a second volume from the three-dimensional image information;
wherein
the first volume is an entire volume of the one cell aggregation; and
the second volume is a volume of a cavity part of the one cell aggregation; and
(e) determines a culture state of the at least one cell aggregation using the first volume and the second volume.

The method for determining a culture state of the present disclosure comprises:

(a) repeatedly causing an image sensor to acquire a captured image including a cell aggregation when the cell aggregation is illuminated with each of a plurality of light sources sequentially, to acquire a plurality of captured images;

wherein each of the plurality of the captured images includes the cell aggregation, (b) extracting an image region including the cell aggregation from each of the plurality of the captured images;

(c) generating three-dimensional image information with regard to the image region with the plurality of the captured images;

(d) calculating a first volume and a second volume from the three-dimensional image information;

wherein the first volume is an entire volume of the cell aggregation; and the second volume is a volume of a cavity part of the cell aggregation; and (e) determining a culture state of the cell aggregation using the first volume and the second volume.

Another method for determining a culture state of the present disclosure comprises:

(a) repeatedly causing an image sensor to acquire a captured image including at least one cell aggregation included in a plurality of cell aggregations when the plurality of the cell aggregations are illuminated with each of a plurality of light sources sequentially, to acquire a plurality of captured images;

wherein each of the plurality of the captured images includes the at least one cell aggregation included in the plurality of the cell aggregations, (b) extracting an image region including one cell aggregation from each of the plurality of the captured images;

(c) generating three-dimensional image information with regard to the image region with the plurality of the captured images;

(d) calculating a first volume and a second volume from the three-dimensional image information;

wherein the first volume is an entire volume of the one cell aggregation; and the second volume is a volume of a cavity part of the one cell aggregation; and (e) determining a culture state of the at least one cell aggregation using the first volume and the second volume.

The comprehensive or specific aspect described above may be realized by a system, a device, a method, an integrated circuit, a computer program, or a recording medium such as a computer-readable recording disk. The comprehensive or specific aspect described above may be realized by any combination of the system, the device, the method, the integrated circuit, the computer program and the recording medium. The computer-readable recording medium includes a non-volatile recording medium such as a compact disc-read only memory (i.e., CD-ROM).

The present disclosure allows a state of one or more cell aggregation to be evaluated.

BRIEF DESCRIPTION OF THE DRAWINGS

FIG. 4 is a diagram illustrating one example of contents stored in a storage unit according to the first embodiment.

FIG. 5 is a diagram illustrating one example of the contents stored in the storage unit according to the first embodiment.

FIG. 8 is a diagram illustrating one example of the contents stored in the storage unit according to the first embodiment.

FIG. 9C is a diagram illustrating one example of a processed image of the spheroid region.

FIG. 10 is a diagram illustrating one example of the contents stored in the storage unit according to the first embodiment.

FIG. 23 is a diagram illustrating one example of contents stored in a storage unit according to the second embodiment, regarding information on the spheroid region.

DETAILED DESCRIPTION OF THE EMBODIMENT

Figure 1:
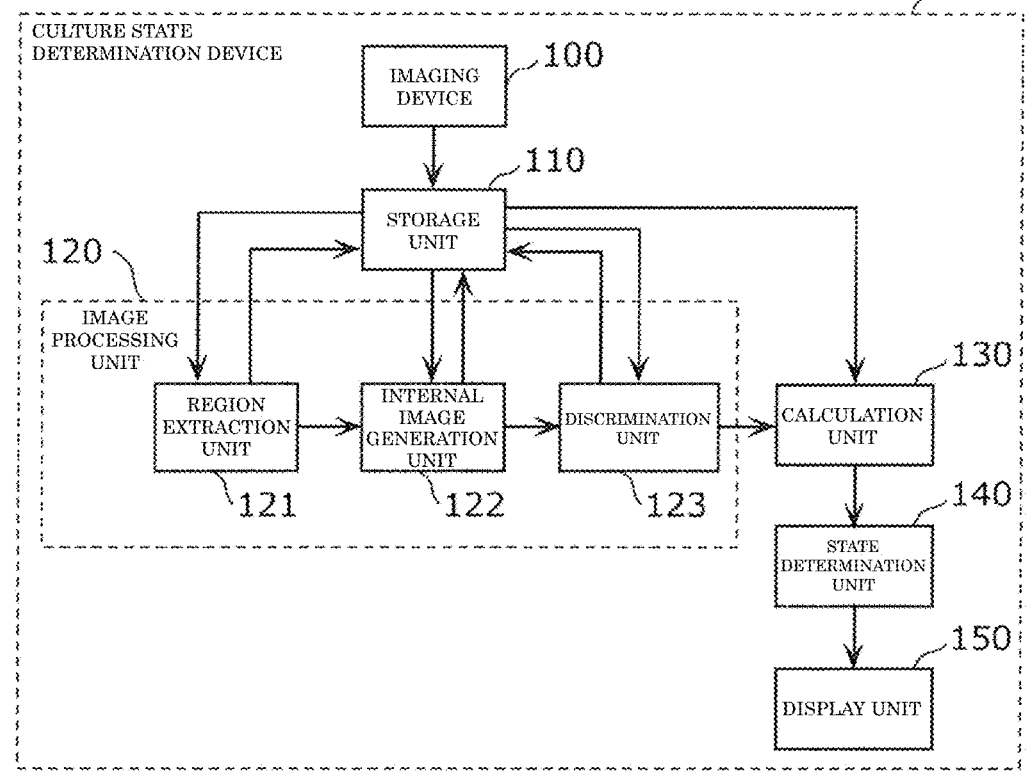
FIG. 1 is a block diagram illustrating one example of a functional configuration of a culture state determination device according to a first embodiment.

The inventors related to the present disclosure, namely, the present inventors have reached the following findings. When cells are cultured for medical or industrial purposes, a large amount of spheroids are produced simultaneously. The quality of the large amount of the spheroids is determined in a state where the large amount of the spheroids are contained in a culture vessel such as the same well as one another. As described in the section of "Background", if the conventional techniques disclosed in Patent Literatures 1 to 3 are used, each spheroid is individually determined. In the above prior art, a lot of time and processing amounts are required to evaluate the quality of all spheroids. For this reason, the present inventors have considered a technique that makes it possible to evaluate the internal state of one or more spheroids together. For example, the present inventors have considered a technique that enables an image of one or more cell aggregation such as spheroids in the same culture vessel to be simultaneously captured, and the internal state of all the cell aggregations to be evaluated from the captured image. As a result, the present inventors have devised a technique as shown below.

For example, the culture state determination device of one aspect of the present disclosure comprises:
a plurality of light sources;
an image sensor on which a cell aggregation is to be mounted; and
control circuitry which, in operation,
(a) repeatedly causes the image sensor to acquire a captured image including the cell aggregation when the cell aggregation is illuminated with each of the plurality of the light sources sequentially, to acquire a plurality of captured images;
wherein
each of the plurality of the captured images includes the cell aggregation,
(b) extracts an image region including the cell aggregation from each of the plurality of the captured images;
(c) generates three-dimensional image information with regard to the image region with the plurality of the captured images;
(d) calculates a first volume and a second volume from the three-dimensional image information;
wherein
the first volume is an entire volume of the cell aggregation; and
the second volume is a volume of a cavity part of the cell aggregation; and
(e) determines a culture state of the cell aggregation using the first volume and the second volume.

The culture state determination device of another aspect of the present disclosure comprises:
a plurality of light sources;
an image sensor on which a plurality of cell aggregations are to be mounted; and
control circuitry which, in operation,
(a) repeatedly causes the image sensor to acquire a captured image including at least one cell aggregation included in the plurality of the cell aggregations when the plurality of the cell aggregations are illuminated with each of the plurality of the light sources sequentially, to acquire a plurality of captured images;
wherein
each of the plurality of the captured images includes the at least one cell aggregation included in the plurality of the cell aggregations,
(b) extracts an image region including one cell aggregation from each of the plurality of the captured images;
(c) generates three-dimensional image information with regard to the image region with the plurality of the captured images;
(d) calculates a first volume and a second volume from the three-dimensional image information;
wherein
the first volume is an entire volume of the one cell aggregation; and
the second volume is a volume of a cavity part of the one cell aggregation; and
(e) determines a culture state of the at least one cell aggregation using the first volume and the second volume.

The method for determining a culture state of one aspect of the present disclosure comprises:
(a) repeatedly causing an image sensor to acquire a captured image including a cell aggregation when the cell aggregation is illuminated with each of a plurality of light sources sequentially, to acquire a plurality of captured images;
wherein
each of the plurality of the captured images includes the cell aggregation,
(b) extracting an image region including the cell aggregation from each of the plurality of the captured images;
(c) generating three-dimensional image information with regard to the image region with the plurality of the captured images;
(d) calculating a first volume and a second volume from the three-dimensional image information;

wherein the first volume is an entire volume of the cell aggregation; and the second volume is a volume of a cavity part of the cell aggregation; and (e) determining a culture state of the cell aggregation using the first volume and the second volume.

The method for determining a culture state of another aspect of the present disclosure comprises:

(a) repeatedly causing an image sensor to acquire a captured image including at least one cell aggregation included in a plurality of cell aggregations when the plurality of the cell aggregations are illuminated with each of a plurality of light sources sequentially, to acquire a plurality of captured images;

wherein each of the plurality of the captured images includes the at least one cell aggregation included in the plurality of the cell aggregations, (b) extracting an image region including one cell aggregation from each of the plurality of the captured images;

(c) generating three-dimensional image information with regard to the image region with the plurality of the captured images;

(d) calculating a first volume and a second volume from the three-dimensional image information;

wherein the first volume is an entire volume of the one cell aggregation; and the second volume is a volume of a cavity part of the one cell aggregation; and (e) determining a culture state of the at least one cell aggregation using the first volume and the second volume.

The comprehensive or specific aspect described above may be realized by a system, a device, a method, an integrated circuit, a computer program, or a recording medium such as a computer-readable recording disk. The comprehensive or specific aspect described above may be realized by any combination of the system, the device, the method, the integrated circuit, the computer program and the recording medium. The computer-readable recording medium includes a non-volatile recording medium such as a CD-ROM. In addition, a device may be configured by one or more devices. If a device is configured by two or more devices, the two or more devices may be disposed in one device or may be separately disposed in two or more separated devices. In the present specification and claims, a "device" can mean not only a single device, but also a system consisting of a plurality of devices.

Hereinafter, the culture state determination device according to the present disclosure will be specifically described with reference to the drawings. Each of the embodiments described below shows a comprehensive or specific example. Numerical values, shapes, components, arrangement positions and connection forms of components, steps, order of the steps, and the like that will be shown in the following embodiments are merely examples, and are not intended to limit the present disclosure. In addition, among the constituent elements in the following embodiments, constituent elements that are not described in the independent claims indicating the highest concept are described as optional constituent elements. Each drawing is a schematic diagram and is not necessarily illustrated accurately. Furthermore, in each figure, the same reference signs are assigned with regard to the substantially same components, and the redundant description may be omitted or simplified.

First Embodiment

Figure 2:
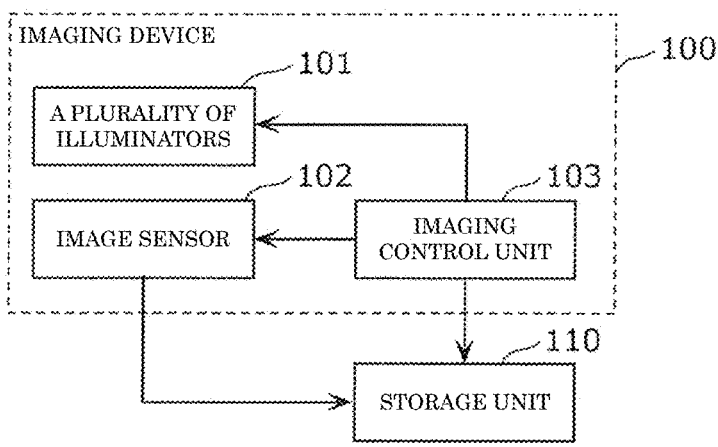
FIG. 2 is a block diagram illustrating one example of a functional configuration of an imaging device of FIG. 1.

A culture state determination device 10 according to the first embodiment will be described. FIG. 1 shows a block diagram of one example of a functional configuration of the culture state determination device 10 according to the first embodiment. FIG. 2 is a block diagram illustrating one example of a functional configuration of an imaging device 100 in FIG. 1. As shown in FIGS. 1 and 2, the culture state determination device 10 according to the first embodiment illuminates sequentially a plurality of spheroids that are a plurality of objects positioned on an image sensor 102 with a plurality of illuminators 101 disposed above the image sensor 102, captures images of the plurality of the spheroids together using the image sensor 102 for each illumination, and acquires a plurality of captured images. Furthermore, the culture state determination device 10 uses the acquired plurality of the captured images to generate images of the plurality of the spheroids in an arbitrary virtual focal plane located between the plurality of the illuminators 101 and the image sensor 102. An image on the arbitrary virtual focal plane generated using the plurality of the captured images in this way is referred to as a "in-focus image". The culture state determination device 10 determines the volume of the spheroid based on the outer shape of the spheroid and the volume of the cavity part in the spheroid in the generated in-focus image, and determines the quality of the state of the culture of the spheroid based on the two volume ratio. The volume of the spheroid can be replaced with the number of cells corresponding to the volume, and the volume of the cavity part can be replaced with the number of cells corresponding to the volume. The number of cells thus replaced is referred to as "pseudo cell number".

1-1. Configuration of Culture State Determination Device According to First Embodiment The configuration of the culture state determination device 10 according to the first embodiment will be described. As shown in FIG. 1, the culture state determination device 10 comprises an imaging device 100, a storage unit 110, an image processing unit 120, a calculation unit 130, a state determination unit 140, and a display unit 150. Further, the image processing unit 120 comprises a region extraction unit 121, an internal image generation unit 122, and a discrimination unit 123.

First, the configuration of the imaging device 100 will be described. As illustrated in FIG. 2, the imaging device 100 comprises a plurality of illuminators 101, an image sensor 102, and an imaging control unit 103. The imaging device 100 acquires a captured image (photographic image) of the object using the image sensor 102. In the present embodiment, the imaging device 100 does not have a focus lens. The imaging device 100 may be formed by one device or system, may be formed by a plurality of devices or systems, and may be incorporated in a device or system other than other constituent elements of the culture state determination device 10. Here, the illuminators 101 are one example of a light source.

The object is, for example, a plurality of spheroids put on the image sensor 102. Each spheroid is a cell aggregation composed of a plurality of translucent cells and has a three-dimensional structure. In other words, in the spheroid, the plurality of the cells may be positioned in a threedimensionally overlapping way. Such a spheroid is translucent and light can pass through the spheroid. For example, the spheroid has a spherical or elliptical outer shape and has a maximum diameter of not more than 200 μm. Here, the spheroid is an example of the cell aggregation.

Each of the plurality of the illuminators 101 outputs diffused light. The plurality of the illuminators 101 may be a plurality of illumination devices such as light-emitting-diodes (i.e., LEDs), may be a plurality of light sources, and may be a plurality of light emitting elements of displays. Each illuminator 101 emits light that does not intersect. A plurality of light rays representing light emitted from one illuminator included in the illuminators 101 do not cross each other. For example, regarding a first illuminator and a second illuminator, both of which are included in the plurality of the illuminators 101, each of the first illuminator and the second illuminator emits light that does not intersect each other. In other words, a plurality of first light rays representing the first light emitted from the first illuminator do not intersect each other. In addition, a plurality of second light rays representing the second light emitted from the second illuminator do not intersect each other. Accordingly, when light is emitted from either the first illuminator or the second illuminator, the light from the first illuminator or the second illuminator reaches one sensor pixel included in the image sensor 102 from a single direction. In other words, the light emitted from each illuminators 101 does not enter one sensor pixel of the image sensor 102 from two or more directions. The image sensor 102 has a plurality of sensor pixels arranged along the light receiving surface thereof.

Such illumination light can be realized by diffused light from the illuminators 101 each having a point-shaped light emitting unit, and can also be realized by light from the illuminators 101 each of which emits parallel light. For example, the illuminators 101 each having a point-shaped light emitting unit may be substituted by a pseudo point light source. An example of a plurality of the pseudo point light source is provided by putting a light-shielding plate having a plurality of pinholes at the vicinity of one illuminating device. Light emitted from the illumination device passes through the pinhole which is open and reaches the image sensor 102. The light emitted from the pinhole mimics light emitted from the point light source. The position of the pseudo point light source, namely, the illumination position, can be changed by changing the pinhole to be opened. The size of each of the pinholes is limited by the pitch of the sensor pixels of the image sensor 102, the distance between the image sensor 102 and the pinholes, and the distance from the image sensor 102 at which the in-focus image is generated.

Figure 3:
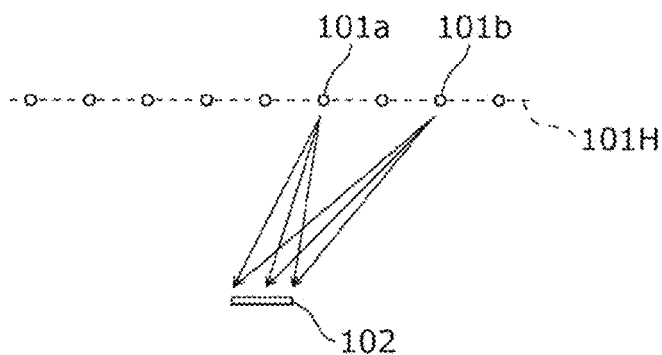
FIG. 3 is a side view schematically showing one example of a relationship between a plurality of illuminators and an image sensor in the culture state determination device according to the first embodiment.

The plurality of the illuminators 101 are arranged above the light receiving surface of the image sensor 102 and emit light downwards. The plurality of the illuminators 101 are arranged side by side along the plane, and sequentially emit light. The plurality of the illuminators 101 are arranged at different positions when viewed from the image sensor 102, and emit light in such a way that the rays of the light travel from different directions to the object on the image sensor 102. For example, the plurality of the illuminators 101 may be configured as shown in FIG. 3. FIG. 3 is a side view schematically showing one example of a relationship between the plurality of the illuminators 101 and the image sensor 102 in the imaging device 100 according to the first embodiment. In this case, the plurality of the illuminators 101 are arranged at different positions, for example, in a grid arrangement, on a single plane 101H which is parallel to a surface which is the light receiving surface of the image sensor 102. Such a plurality of the illuminators 101 emit light in such a way that the rays of the light travel from different directions to the object on the image sensor 102. For example, light emitted from a first illuminator 101a and a second illuminator 101b included in the plurality of the illuminators 101 is incident on the object on the image sensor 102 from different directions. In addition, the light emitted from each of the first illuminator 101a and the second illuminator 101b reach one sensor pixel of the image sensor 102 from the single direction.

As described above, the light emitted from the plurality of the illuminators 101 arranged at different positions with respect to the light receiving surface of the image sensor 102 is incident on the light receiving surface at different incident angles. Furthermore, the incident direction of light with respect to the same sensor pixel of the image sensor 102 differs for each illuminator 101. Here, the illuminators 101 are examples of a light source.

In the present embodiment, the plurality of the illuminators 101 are the plurality of the point light sources arranged on the plane 101H. However, as shown in Patent Literature 4, the plurality of the illuminators 101 may be composed of a plurality of light sources which are arranged on a spherical surface and emit parallel light.

The image sensor 102 has a plurality of sensor pixels. Each sensor pixel of the image sensor 102 is arranged on the light receiving surface, and acquires intensity of light emitted from the plurality of the illuminators 101. The image sensor 102 acquires a captured image based on the intensity of the light acquired by each sensor pixel. Note that "the image sensor 102 captures an image (also referred to as "photographs")" means that the image sensor 102 detects and records the intensity of the light incident on each sensor pixel. When the spheroid is put as an object on the light receiving surface of the image sensor 102, the image sensor 102 acquires the intensity of the light which has passed through the spheroid. The image sensor 102 stores information on the acquired captured image in the storage unit 110. An example of the image sensor 102 is a complementary metal-oxide semiconductor (i.e., CMOS) image sensor or a charge coupled device (i.e., CCD) image sensor.

The imaging control unit 103 controls emitting of light by the plurality of the illuminators 101 and capturing images by the image sensor 102. Specifically, the imaging control unit 103 controls the order in which the plurality of the illuminators 101 emit light, the time intervals at which the plurality of the illuminators 101 emit light, and the like. The imaging control unit 103 associates information on the captured image such as an ID (Identification), a capturing time, and the illuminator which is included in the illuminators 101 and emits light with the captured image data captured by the image sensor 102 and stores the information in the storage unit 110.

The imaging control unit 103 may be configured with a computer system (not shown) including a processor such as a central processing unit (i.e., CPU) or a digital signal processor (i.e., DSP), and a memory such as a random access memory (i.e., RAM) and a read-only memory (i.e., ROM). A part or the entire of the functions of the constituent elements of the imaging control unit 103 may be achieved by the CPU or the DSP executing the program recorded in the ROM using the RAM as a temporary memory. In addition, the part or the entire of the functions of the constituent elements of the imaging control unit 103 may be achieved by a dedicated hardware circuit such as an electronic circuit or an integrated circuit. The part or the entire of the functions of the constituent elements of the imaging control unit 103 may be configured by a combination of the above software function and hardware circuit. The program may be provided as an application through communication via a communication network such as the Internet, communication according to a mobile communication standard, other wireless network, wired network, or broadcast. Here, the imaging control unit 103 is one example of control circuitry.

Furthermore, constituent elements other than the imaging device 100 will be described. The storage unit 110 is realized by a storage device such as a semiconductor memory such as a ROM, a RAM, or a flash memory, a hard disk drive, or a solid state drive (i.e., SSD), for example. The storage unit 110 stores the plurality of the captured images acquired by the imaging device 100. The storage unit 110 stores the images captured by the image sensor 102 together with position information on the illuminator which is included in the illuminators 101 and has been used for the capture of the images.

For example, FIG. 4 shows one example of contents stored in the storage unit 110 as described above. For each captured image file acquired by the imaging device 100, the position information on the illuminator which is included in the illuminators 101 and has been used for acquiring the captured image file, namely, the illumination position is stored. In the example of FIG. 4, the illumination position indicates relative positions of the illuminators 101 with respect to the image sensor 102. Hereinafter, the position information of the illuminators 101 is also referred to as "illumination position information", and the position of the illuminators 101 is also referred to as "illumination position". The illumination position information is stored together with or associated with the file ID of the captured image file, and is combined with the captured image file via the file ID. Note that the illumination position information may be recorded in a part of the captured image file (for example, as header information).

The image processing unit 120 is realized by the control circuitry. As illustrated in FIG. 1, the image processing unit 120 comprises the region extraction unit 121, the internal image generation unit 122, and the discrimination unit 123. The image processing unit 120 may be formed by a single device or system, may be formed by a plurality of devices or systems, and may be incorporated in a device or system other than other components of the image processing unit 120.

The region extraction unit 121 extracts a region where an image of the spheroid that is an object is present from at least one captured image included in a plurality of captured images which have been captured by the imaging device 100 and stored in the storage unit 110. In other words, the region extraction unit 121 extracts a region of the spheroid. In the present embodiment, the region extraction unit 121 extracts the region only from one captured image; however, is not limited to this. An image from which the region is extracted is referred to as a "reference captured image".

Specifically, in the present embodiment, from the captured images corresponding to the positions of the illuminators 101, the region extraction unit 121 determines, as the reference captured image, an image captured when the illuminator which is included in the illuminators 101 and has been located immediately above the center position of the light receiving surface of the image sensor 102 emits light. Furthermore, the region extraction unit 121 extracts the region of the spheroid in the reference captured image. An extraction method of the region is based on, for example, a known image recognition processing. The region extraction unit 121 determines, as a target region, a region extracted based on the result of the image recognition for one reference captured image. The recognition processing of the region of the spheroid is performed based on features such as a predetermined color and outline, for example. If a plurality of regions are extracted by recognition processing of the region of the spheroid, the region extraction unit 121 determines all of the plurality of the extracted regions as the target regions. The region extraction unit 121 stores the determined target region in the storage unit 110 in association with the reference captured image from which the target region has been extracted. The reference captured image is not limited to an image captured at the time when the illumination of the illuminators 101 located immediately above the center position of the light receiving surface of the image sensor 102 emits light, and the reference captured image may be any captured image of the illuminators 101. For example, the reference captured image may be an image captured on the light receiving surface of the image sensor 102 at the time when the illumination of the illuminators 101 located immediately above a region where the spheroid density is high.

For example, FIG. 5 illustrates one example of the contents stored in the storage unit 110 as described above. The region extraction unit 121 assigns, for example, a region ID to each of one or more spheroid regions determined as the target region. Furthermore, the region extraction unit 121 calculates coordinates on the reference captured image, for example, pixel coordinates, for each region corresponding to the region ID. The pixel coordinates are a coordinate system based on pixels in an image. As illustrated in FIG. 5, the region extraction unit 121 associates the coordinates of each region with the region ID corresponding to each region, and stores these in the storage unit 110. Note that any method may be used to set the coordinates of the spheroid region. For example, the region extraction unit 121 may form a rectangular frame or the like circumscribing the spheroid region on the reference captured image, and may set the coordinates of one or more points on the frame as the coordinates of the region. In this case, the region extraction unit 121 may also store information on the size of the frame such as the side length in the storage unit 110 in association with the region ID. Alternatively, the region extraction unit 121 may use the coordinates of the center of gravity of the spheroid region on the reference captured image as the coordinates of the region. In the example of FIG. 5, the coordinates of the spheroid region are the coordinates of the two vertices at the diagonal position of the rectangular frame.

The internal image generation unit 122 generates an internal image of the one or more spheroids. The internal image generation unit 122 performs refocusing processing in accordance with position information on a predetermined virtual focal plane using the plurality of the captured images and the illumination position information stored in the storage unit 110, to generate an in-focus image of the spheroid at the focal plane. The internal image generation unit 122 generates an in-focus image for each virtual focal plane. The internal image generation unit 122 stores the generated in-focus image in the storage unit 110. The processing for generating the in-focus image is referred to as "refocusing processing", and details of the refocusing processing will be described later.

Figures 6, 7:
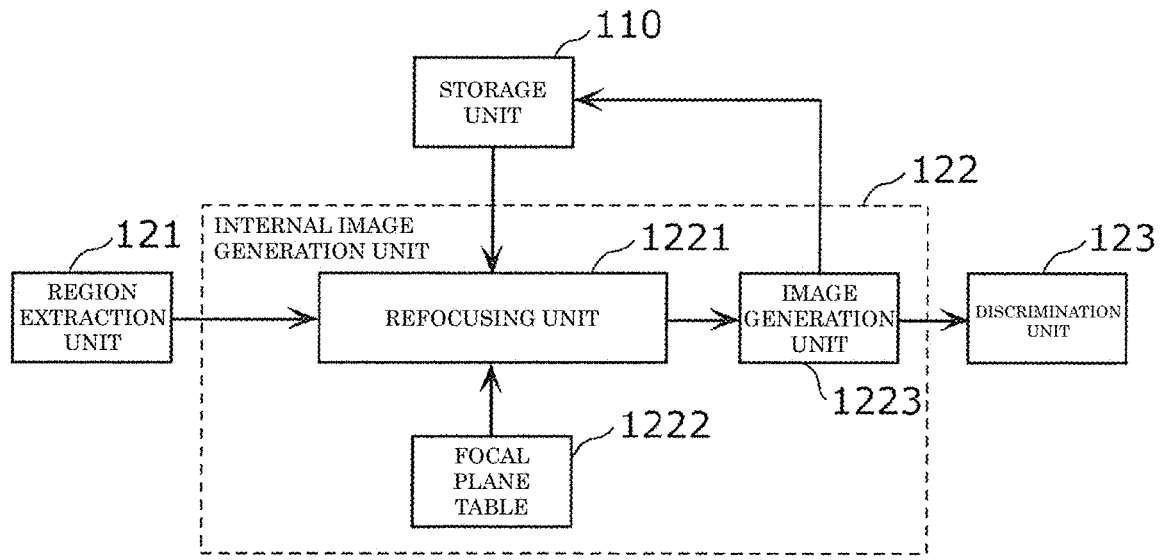
FIG. 6 is a block diagram illustrating one example of a functional configuration of an internal image generation unit according to the first embodiment.
FIG. 7 is a diagram illustrating one example of contents stored in a focal plane table according to the first embodiment.

Further, FIG. 6 shows a detailed configuration of the internal image generation unit 122. FIG. 6 is a block diagram illustrating one example of a functional configuration of the internal image generation unit 122 according to the first embodiment. As shown in FIG. 6, the internal image generation unit 122 comprises a refocusing unit 1221, a focal plane table 1222, and an image generation unit 1223.

The focal plane table 1222 stores a position of the predetermined virtual focal plane. The focal plane table 1222 may have any of the configurations described above regarding the storage unit 110. The virtual focal plane is a focal plane located between the plurality of the illuminators 101 and the image sensor 102. In this embodiment, the virtual focal plane is a plane parallel to the light receiving surface of the image sensor 102; however, may be a surface in a direction intersecting with the light receiving surface. For example, FIG. 7 shows one example of the contents stored in the focal plane table 1222. An ID is assigned to each focal plane for a plurality of the predetermined virtual focal planes. The distance between each focal plane and the surface of the image sensor, that is, the light receiving surface, is stored in the focal plane table 1222 together with the ID of the focal plane. In the example of FIG. 7, all of the virtual focal planes are planes parallel to the surface of the image sensor 102. For example, in the example of FIG. 7, 200 virtual focal planes are set at intervals of 1 μm so as to cover the entire of the spheroid. As described above, the focal planes may be equally or unequally spaced.

The refocusing unit 1221 generates focused pixels each forming the in-focus image on the virtual focal plane for all of one or more spheroid regions extracted by the region extraction unit 121. In the present embodiment, the pixels forming the in-focus image are referred to as "focused pixels". The refocusing unit 1221 can generate the focused pixels of the in-focus image on the focal plane from the plurality of the captured images, the position information on the plurality of the illuminators 101, and the position information on the virtual focal plane. Specifically, the refocusing unit 1221 identifies the pixels in the captured image on which the focused pixels of the in-focus image are projected based on the plurality of the captured images and the position information on the illuminator which is included in the illuminators 101 and illuminated when each of the captured images was captured. And then, the refocusing unit 1221 calculates the pixel value of the focused pixel using the pixel value of the identified pixel. The refocusing unit 1221 calculates a pixel value for each focused pixel. This makes it possible to generate the in-focus image. Examples of pixel values are light intensity and luminance value.

In the present embodiment, the refocusing unit 1221 does not generate focused pixels at all pixel positions on the virtual focal plane. The refocusing unit 1221 generates only focused pixels in all the spheroid regions. Specifically, the refocusing unit 1221 calculates the pixel coordinates of the regions of all the spheroids on the in-focus images on the virtual focused plane from the pixel coordinates of the regions of all the spheroids extracted by the region extraction unit 121 as illustrated in FIG. 5. Furthermore, the refocusing unit 1221 generates only focused pixels included in each region of the spheroid on the in-focus image. In the present embodiment, the pixel coordinate system of the region of the spheroid extracted by the region extraction unit 121 and the pixel coordinate system of the in-focus image of the virtual focal plane are the same as each other. Therefore, the generation processing of the focused pixel is simplified.

When the focused pixel on the virtual focal plane is generated, the refocusing unit 1221 calculates a position on the image sensor 102, which light emitted by each of the illuminators 101 reaches through a focal point, from the focal point at the position of the focused pixel and the illumination position information corresponding to each captured image. The focal point is a point on the virtual focal plane. Further, on the captured image corresponding to each of the illuminators 101, namely, each of the illumination positions, the refocusing unit 1221 extracts a pixel value at the pixel position corresponding to the position, based on the position which the light of the illuminators 101 reaches on the image sensor 102. This pixel value is a pixel value indicating the in-focus image. Then, the refocusing unit 1221 adds all the pixel values indicating the in-focus image extracted in the captured images corresponding to each illumination position. Thereby, a pixel value in which the luminance of all of the light which are incident from different directions and pass through the focal point has been integrated is provided. The pixel value is set as the pixel value of the focused pixel. In this way, the refocusing unit 1221 generates focused pixel information on the focal point, and performs the above-described processing on each focused pixel on the in-focus image. This makes it possible to generate the in-focus image of the region of the spheroid. The above method is the same as the refocusing technique described in Patent Literature 4. Since the technique of Patent Literature 4 is known, the detailed description is omitted.

The image generation unit 1223 generates each of in-focus images of all regions of the spheroids on the focal planes based on the focused pixel information of the focal point generated by the refocusing unit 1221. The image generation unit 1223 stores the generated in-focus images in the storage unit 110 in association with the focal plane position information and the ID of the region of the spheroid corresponding to the in-focus image.

For example, FIG. 8 illustrates one example of the contents stored in the storage unit 110 as described above. The internal image generation unit 122 sets an ID for each in-focus image in the region of the spheroid. This ID is also associated with the focal plane including the in-focus image, and is referred to as "focal plane image ID". For each region of the spheroid, the internal image generation unit 122 stores a file of the in-focus image of the region of the spheroid at each of the plurality of predetermined focal planes and the focal plane image ID corresponding to the file in the storage unit 110 in association with the position information on the focal plane including the in-focus image, and in association with the ID and the coordinate of the region of the spheroid. In the example of FIG. 8, the focal plane position information indicates the distance from the surface of the image sensor 102. The focal plane position information is combined with the file of the in-focus image via the focal plane image ID. The focal plane position information may be recorded in a part of the file of the in-focus image (for example, header information).

The discrimination unit 123 discriminates the outer shape of the spheroid that is the object from the cavity part in the inside of the spheroid on the basis of the pixel value for each in-focus image stored in the storage unit 110.

Figure 9A:
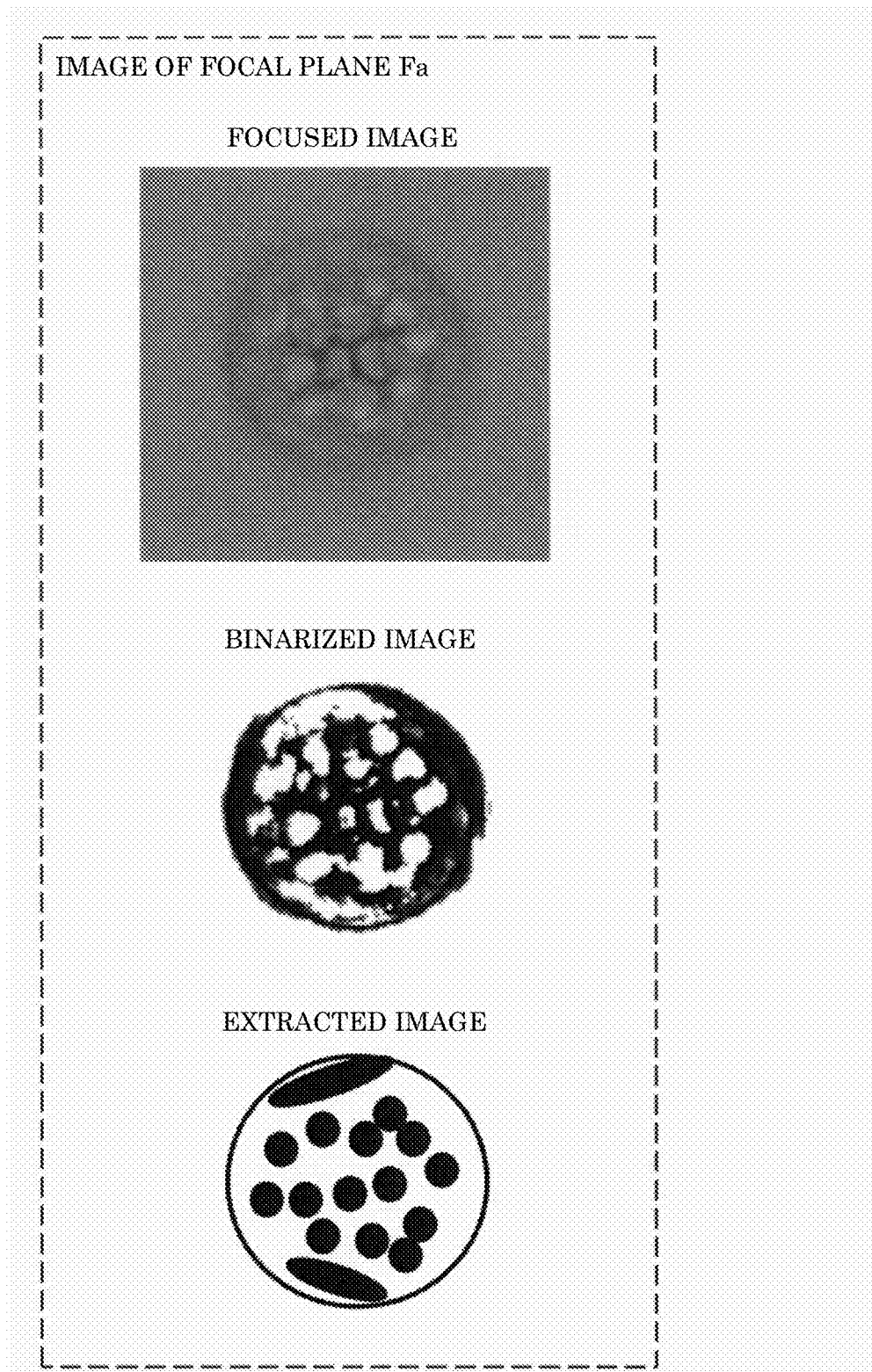
FIG. 9A is a diagram illustrating one example of a processed image of a spheroid region.
Figure 9B:
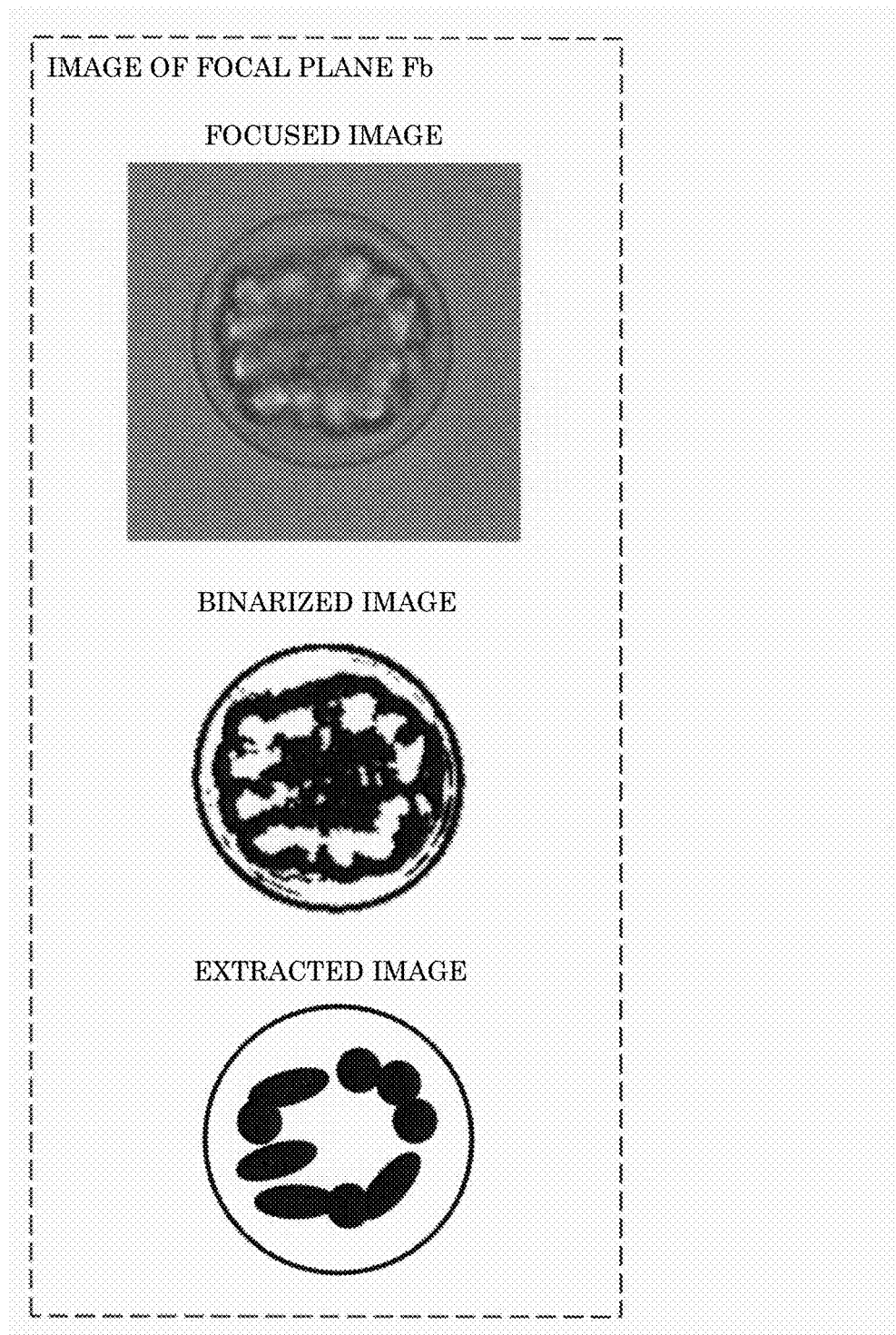
FIG. 9B is a diagram illustrating one example of a processed image of the spheroid region.
Figure 9D:
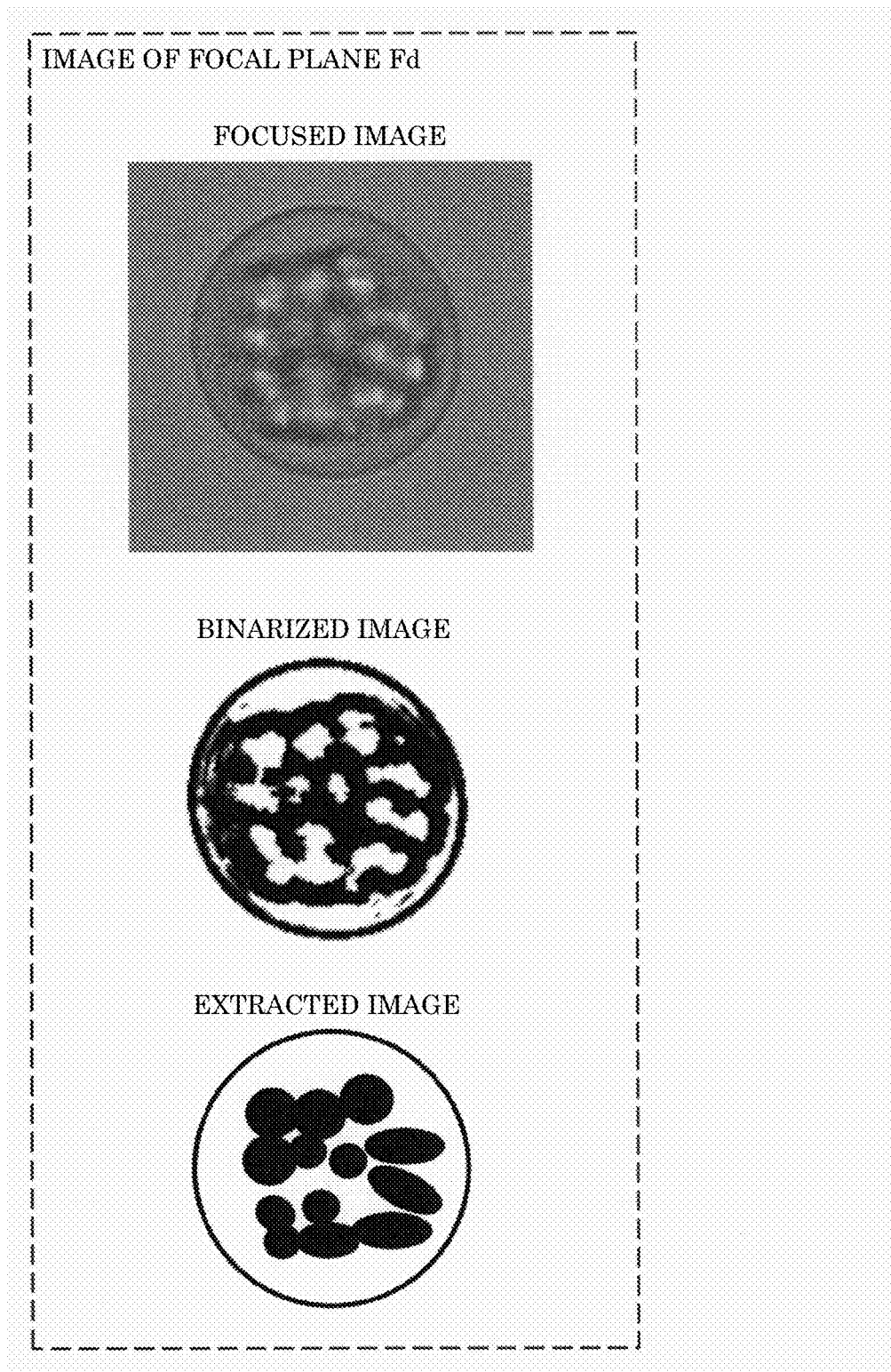
FIG. 9D is a diagram illustrating one example of a processed image of the spheroid region.

For example, FIGS. 9A to 9D schematically show examples of the plurality of the in-focus images at different focal planes Fa to Fd for the same spheroid region. FIG. 9A to 9D are diagrams showing examples of processed images of the region of the spheroid. The in-focus images are upper images in FIGS. 9A to 9D. The distance between the focal planes Fa to Fd and the surface of the image sensor 102 are increased from FIG. 9A to FIG. 9D. In other words, the focal plane Fa in FIG. 9A is closest to the surface of the image sensor 102. In the in-focus image of FIG. 9A, the entire image is blurred; however, the outer shape of the spheroid can be extracted by extracting a part darker than the periphery, namely, a part having a small pixel value. In the in-focus image of FIG. 9B, the part darker than the periphery is extracted as the outer shape of the spheroid, and the part darker than other parts in the outer shape of the spheroid, namely, a part having a smaller pixel value can be extracted as the cavity part. In the in-focus images of FIGS. 9C and 9D, similarly to the case of FIG. 9B, the outer shape of the spheroid and the cavity part in the inside of the spheroid can be extracted.

The discrimination unit 123 calculates, in each in-focus image, the number of first pixels that are determined to be present in the inside of the outer shape of each spheroid and the number of second pixels that are determined to be present in the cavity part in the spheroid. The first pixel can include the second pixel. In one in-focus image of the spheroid, the number of the first pixels may correspond to the area in the inside of the outer shape of the spheroid, and the number of the second pixels may correspond to the area of the cavity part of the spheroid. The sum of the numbers of the first pixels of all the in-focus images corresponding to one spheroid corresponds to the volume in the inside of the outer shape of the spheroid, and the sum of the numbers of the second pixels of all the in-focus images corresponding to one spheroid may correspond to the volume of the cavity part of the spheroid. The discrimination unit 123 stores the numbers of the first pixel and the second pixel of each in-focus image in the storage unit 110 in association with the focal plane image ID of the in-focus image. Here, the number of the first pixels is one example of the first area, and the number of the second pixels is one example of the second area.

For example, FIG. 10 illustrates one example of the contents stored in the storage unit 110 as described above. For each in-focus image corresponding to the plurality of the focal planes in the region of each spheroid, the discrimination unit 123 stores the numbers of the first pixels and the second pixels in association with the ID of the region of the spheroid, the focal plane image ID of the in-focus image, and the position information on the focal plane of the in-focus image in the storage unit 110. Thereby, for example, on the three-dimensional coordinates defined by the x-axis and y-axis, which are included in the surface of the image sensor 102, and the z-axis, which is perpendicular to the surface, it is possible to calculate the distribution of the first pixels in the inside of the spheroid and the distribution of the second pixels of the cavity part in the spheroid.

The calculation unit 130 calculates a first total number which is the sum of the number of the first pixels at all the focal planes of all the spheroids and a second total number which is the sum of the number of the second pixels at all the focal planes of all the spheroids from the numbers of the first pixels and the second pixels at each focal plane of each spheroid discriminated by the discrimination unit 123. Furthermore, the calculation unit 130 calculates a first ratio that is a ratio between the first total number and the second total number. The first ratio is indicated by the second total number/the first total number. Here, the first total number is one example of a first volume and a first total volume, and the second total number is one example of a second volume and a second total volume.

The state determination unit 140 compares the first ratio calculated by the calculation unit 130 to a predetermined determination reference value. The state determination unit 140 determines that the culture state of the spheroid is good, if the first ratio is lower than the determination reference value. On the other hand, the state determination unit 140 determines that the culture state of the spheroid is bad, if the first ratio is equal to or greater than the determination reference value. The determination reference value may be set to various values, depending on the type and the amount of cells forming the spheroid, the time point of the culture of the spheroid, the required quality of the culture state of the spheroid, and the use of the spheroid. Such a determination reference value may be determined according to the above conditions by a designer, a manufacturer, or a user of the culture state determination device 10. The determined determination reference value may be input via an input device (not shown) and stored in the storage unit 110. In the present embodiment, as will be described later, the spheroid is a morula of a sea urchin. In this case, an example of the determination reference value is 0.3.

The number of the first pixels in the inside of the spheroid discriminated by the discrimination unit 123 indicates the amount of the cells in the inside of the spheroid, namely, the volume of the cells. The cavity part of the spheroid is a missing part of the cells in the spheroid due to necrosis and the number of the second pixels in the cavity part indicates the amount of cells missing due to the necrosis, namely, the volume of the cells in a pseudo way. For one spheroid, a second ratio, which is the ratio between the sum of the number of the first pixels at all focal planes and the sum of the number of the second pixels at all focal planes, indicates a ratio of the amount of the cells missing due to the necrosis to the total amount of the cells in the one spheroid. Further, the first ratio of the first total number and the second total number indicates the ratio of the amount of cells missing due to the necrosis to the total amount of the cells in the entire of the plurality of the photographed spheroids.

Note that the calculation unit 130 calculates the ratio between the number of the first pixels and the number of the second pixels; however, may calculate a difference provided by subtracting the number of the second pixels from the number of the first pixels. In this case, the state determination unit 140 holds a reference number of pixels as the predetermined determination reference. The state determination unit 140 determines that the culture state is bad if the difference calculated by the calculation unit 130 is equal to or less than the reference number of the pixels. On the other hand, the state determination unit 140 determines that the culture state is good, if the difference exceeds the reference number of the pixels. The difference provided by subtracting the number of the second pixels from the number of the first pixels shows a pseudo amount of normal cells that are not necrotized contained in the spheroid. Also in this case, the calculation unit 130 may calculate a difference provided by subtracting the second total number from the first total number. Similarly to the case of the difference between the number of the first pixel and the number of the second pixel, the state determination unit 140 determines whether the culture state is good or bad for the entire spheroid based on the difference between the first total number and the second total number. In such a case, the state of the spheroids in the entire culture vessel may be determined, and whether or not the spheroids in the culture vessel can be used may be determined. The determination based on the difference as described above is effective, if the number of the spheroids in the culture vessel is known. In addition, the reference of the difference may be based on the determination reference of the first ratio.

The display unit 150 shows the result determined by the state determination unit 140. Examples of the display unit 150 are a display and a speaker. Examples of the display are a liquid crystal panel and an organic or inorganic electroluminescence (i.e., EL). If the display unit 150 is a display, the result can be displayed by characters, symbols, images, and the like. In addition, if the display unit 150 is a speaker, the result may be indicated by a sound and an acoustic signal. The display unit 150 may include one or both of a display and a speaker. The display unit 150 may be other display output means. For example, the display unit 150 may have a configuration that projects onto a wall surface, a glass surface, a space, or the like.

Figure 11:
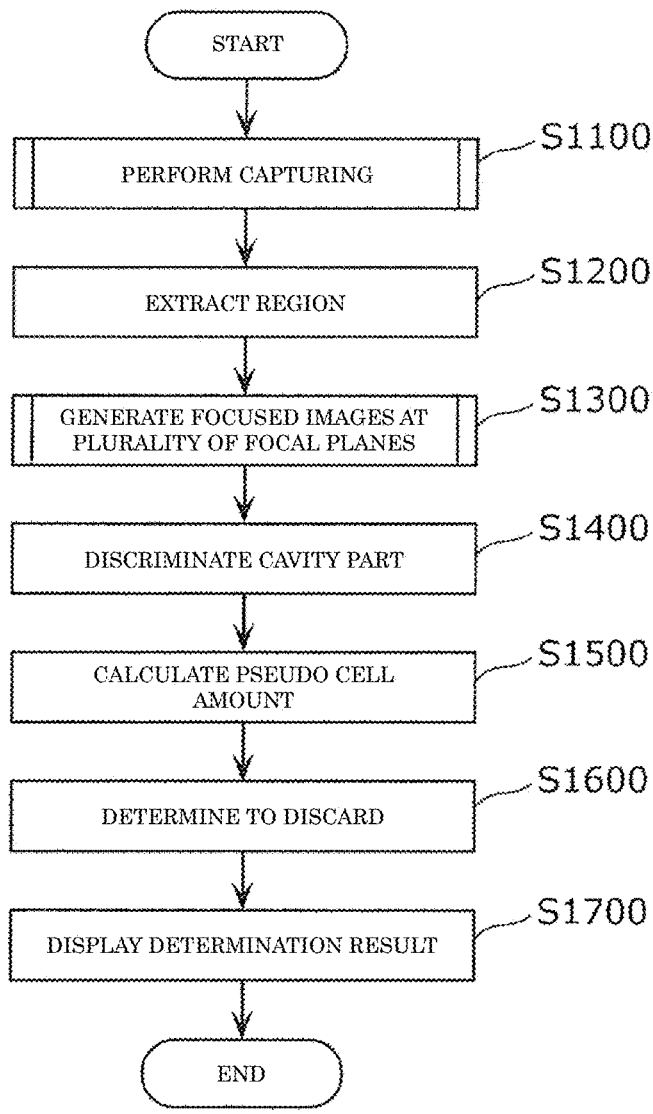
FIG. 11 is a flowchart showing one example of operation of the culture state determination device according to the first embodiment.

1-2. Operation of Culture State Determination Device According to First Embodiment The operation of the culture state determination device 10 according to the first embodiment will be described with reference to FIG. 11. FIG. 11 is a flowchart showing one example of the operation of the culture state determination device 10 according to the first embodiment.

Figure 12:
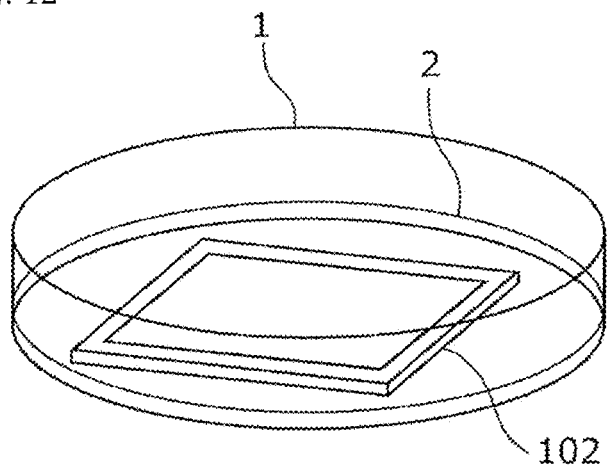
FIG. 12 is a schematic perspective view illustrating one example of a state of capturing an image of the spheroid.

First, in the step S1100, the imaging control unit 103 of the imaging device 100 uses the plurality of the illuminators 101 sequentially to illuminate the plurality of the spheroids that are objects on the image sensor 102, and causes the image sensor 102 to capture a plurality of images of the plurality of the spheroids. For example, as shown in FIG. 12, the plurality of the spheroids are present in a culture solution 2 in a culture vessel 1 such as a well placed on the image sensor 102. FIG. 12 is a schematic perspective view showing one example of the imaging state of spheroids. The imaging control unit 103 causes the image sensor 102 to record the intensity of light which has reached the light receiving surface every time when each of the plurality of the illuminators 101 illuminates the spheroid, to acquire a plurality of captured images on which the entire of the plurality of the spheroids in the culture vessel 1 have been photographed. The imaging control unit 103 stores the captured images in the storage unit 110 in association with the position information on the illuminators 101 illuminated when the captured image is captured. In the present embodiment, the positions of the plurality of the illuminators 101 are fixed with respect to the image sensor 102, and the position information on each of the plurality of the illuminators 101 is determined in advance and stored in the storage unit 110. Details of the imaging processing will be described later.

Next, in the step S1200, the region extraction unit 121 of the image processing unit 120 extracts a region where a spheroid image has been captured, namely, a region of the spheroid, from the captured image acquired in the step S1100. Specifically, the region extraction unit 121 determines one captured image as the reference captured image from among the plurality of the captured images acquired in the step S1100 and stored in the storage unit 110, and acquires the reference captured image and the illumination position information corresponding to the reference captured image from the storage unit 110. The illumination position information is position information on the illuminators 101 illuminated when the reference captured image is captured. The reference captured image is, for example, a captured image at the time of illumination of the illuminators 101 located immediately above the center point of the light receiving surface of the image sensor 102. The region extraction unit 121 extracts one or more spheroid regions based on the pixel value of each pixel in the reference captured image.

An example of the extraction method is to binarize the reference captured image based on a first threshold value set between the maximum value and the minimum value of the pixel values of the reference captured image, and then to divide into a region where the light emitted from the illuminators 101 has reached the light receiving surface of the image sensor 102 directly and a region where the light has passed through the spheroid and has reached the light receiving surface of the image sensor 102.

The first threshold value is a threshold value for distinguishing the region where the spheroid has been photographed from the region where the background of the spheroid has been photographed. The first threshold value may be determined to have various values, depending on conditions such as the type and the amount of the cells forming the spheroid, the time of the culture of the spheroid, and the environment during the capturing of the images. Such a first threshold value may be determined according to the above conditions by the designer, the manufacturer, the user, or the like of the culture state determination device 10, and the determined first threshold value may be input via an input device (not shown) and stored in the storage unit 110. For example, the first threshold value is approximately 50% to 70% of the pixel value between the minimum value and the maximum value of the pixel value of the reference captured image. For example, when (pixel value maximum value)−(pixel value minimum value)=$\alpha$ for all the pixels included in the reference captured image, the first threshold value is may be determined within a range of $0.5\alpha+$(the minimum value of the pixel value)$\leq$(the first threshold value)$\leq 0.7\alpha+$(the minimum value of the pixel value). In addition, in a histogram of the luminance values of the pixels, which is one example showing the distribution of the pixel values in the reference captured image, a pixel having a luminance value with a sharp increase in the number of the pixels may indicate the background of the spheroid. The first threshold value may be determined to be a value equal to or less than such luminance values. The first threshold value may be a value, for example, provided by multiplying the maximum value of the pixel value of the reference captured image by a predetermined ratio. Such a ratio is a value greater than 0 and less than 1, and an example of the ratio is 0.6; however, is not limited thereto.

The region where the image is brighter, namely, the pixel value is equal to or greater than the first threshold value is a region where the light emitted from the illuminators 101 has reached the light receiving surface of the image sensor 102 directly. The region where the image is darker, namely, the pixel value is smaller than the first threshold value is a region where the light has passed through the spheroid and has reached the light receiving surface of the image sensor 102. In the binarized reference captured image, a region where pixels each having a pixel value smaller than the first threshold value continue is determined as a region where the spheroid has been photographed.

The region extraction unit 121 extracts a region where the pixels each having a pixel value smaller than the first threshold value continues in the reference captured image, and determines a minimum rectangular region including the region, for example, a rectangular region circumscribing the region as the region where the image processing will be performed. Furthermore, the region extraction unit 121 sets an ID for the determined rectangular region, and calculates pixel coordinates on the reference captured image of the rectangular region. The region extraction unit 121 stores the pixel coordinates of the rectangular region and the ID of the rectangular region in the storage unit 110 in association with each other. Note that the region extraction unit 121 may calculate the pixel coordinates of at least one vertex of the rectangular region as the pixel coordinates of the rectangular region. Furthermore, the region extraction unit 121 may store the length of the side of the rectangular region in the storage unit 110 as the dimensions of the rectangular region together with the pixel coordinates of the rectangular region. Since one or more spheroids are present in the culture vessel 1, the region of each of the spheroids and the rectangular region thereof are extracted from the reference captured image. In other words, the region of the one or more spheroids and the rectangular regions thereof are extracted.

In the step S1200, the region extraction unit 121 determines a region where pixels each having a pixel value smaller than the first threshold value in the binarized reference captured image as a region where the spheroid has been photographed; however, the region where the spheroid has been photographed may be determined by another method. For example, the region extraction unit 121 may perform edge extraction using a difference in the pixel values between the pixels in the reference captured image, and determine a region surrounded by the edges as a region where the spheroid has been photographed. Alternatively, for example, the region extraction unit 121 may extract a region where pixels each having similar pixel values continue by clustering with the pixel values of the pixels in the reference captured image, and determine the extracted region as a region where the spheroid has been photographed.

Next, in the step S1300, the internal image generation unit 122 of the image processing unit 120 generates the in-focus images at a plurality of the predetermined focal planes, using the plurality of the captured images acquired in the step S1100, for all of the one or more regions of the spheroid determined in the step S1200, namely, for all rectangular regions. In other words, an in-focus image of each rectangular region on each focal plane is generated. Since such an internal image generation unit 122 does not generate an in-focus image in a region other than the rectangular regions, the processing speed for generating the in-focus images can be improved. In the present embodiment, all of the plurality of focal planes are flat surfaces, and each focal plane is parallel to the other focal planes. Further, the plurality of the focal planes are parallel to the light receiving surface of the image sensor 102; however, are not limited thereto. The positions of the plurality of the focal planes are defined using, for example, the distance from the light receiving surface of the image sensor 102 and stored in the storage unit 110 in advance. The plurality of the focused pixels included in the in-focus image on the focal plane correspond one-to-one to a plurality of points on the focal plane. A method for generating an in-focus image will be described later.

Next, in the step S1400, the discrimination unit 123 of the image processing unit 120 extracts the outer shape of the spheroid for each of all the in-focus images generated in the step S1300, based on the pixel value of the in-focus image, and extracts the cavity part in the inside of the outer shape of the spheroid. The discrimination unit 123 discriminates a region of a pixel that is distinguished from other pixels as the cavity part in the inside of the outer shape of the spheroid. The cavity part can be discriminated by, for example, the distribution of the pixel values in the in-focus image.

For example, each of FIGS. 9A to 9D shows an example of a series of processed images of the region of the spheroid. In each of FIGS. 9A to 9D, an in-focus image of the region of the spheroid is shown in the upper part. In the middle part, a binarized image that is a binarized image of the in-focus image in the upper part is shown. In the binarized image, a region where the pixel value is equal to or greater than a second threshold value is indicated as a white region or a non-colored region, and a region where the pixel value is less than the second threshold value is indicated as a black region.

Note that the second threshold value is a threshold value for distinguishing a region where a cell is photographed from a region where the cavity part is photographed in the spheroid. In the binarized images of FIGS. 9A to 9D, the black regions may indicate the cavity parts, and the white regions or the non-colored regions surrounded by the black regions may indicate cells. The white regions or the non-colored regions may indicate cells, and the black regions may indicate the cavity parts. The second threshold value can be determined to have various values, depending on conditions such as the type and the amount of the cells forming the spheroid, the time of the culture of the spheroid, and the environment during the capturing of the images. Such a second threshold value may be determined according to the above conditions by a designer, a manufacturer, or a user of the culture state determination device 10. The determined second threshold value may be input via an input device (not shown) and be stored in the storage unit 110. For example, the second threshold value is a pixel value between approximately 50% to 70% of the pixel value between the minimum value and the maximum value of the pixel value of the in-focus image. For example, with respect to all the pixels included in the in-focus image in the region of the spheroid, when (pixel value maximum value)−(pixel value minimum value)=$\beta$, the second threshold value can be determined within a range of $0.5\beta+$(the minimum value of the pixel value)$\leq$(the second threshold value)$\leq 0.7\beta+$(the minimum value of the pixel value).

In the lower part, an extracted image, which is an image provided by extracting a region of the cell in the binarized image in the middle part, is shown. The image in the lower part schematically shows an image provided by separating regions where the pixels having the pixel values corresponding to the cells are continuous from the binarized image. As described above, FIGS. 9A to 9D are images corresponding to different focal planes Fa to Fd for the same spheroid region as each other, respectively. The spheroid of FIGS. 9A-9D is a sea urchin morulae. The morula is a cell aggregation composed of a plurality of cells of almost the same size as each other, and includes the cavity part at the center.

When discriminating the cavity part in the spheroid, the discrimination unit 123 binarizes the in-focus image as shown in the upper part of FIGS. 9A to 9D to generate a binarized image in the middle part. Further, the discrimination unit 123 labels a region where the pixel value is equal to or greater than the second threshold value on the binarized image, namely, labels the region, and determines a plurality of regions of the cells such as the lower image. In other words, the images in the lower parts are extracted images of the cell region.

Figure 13:
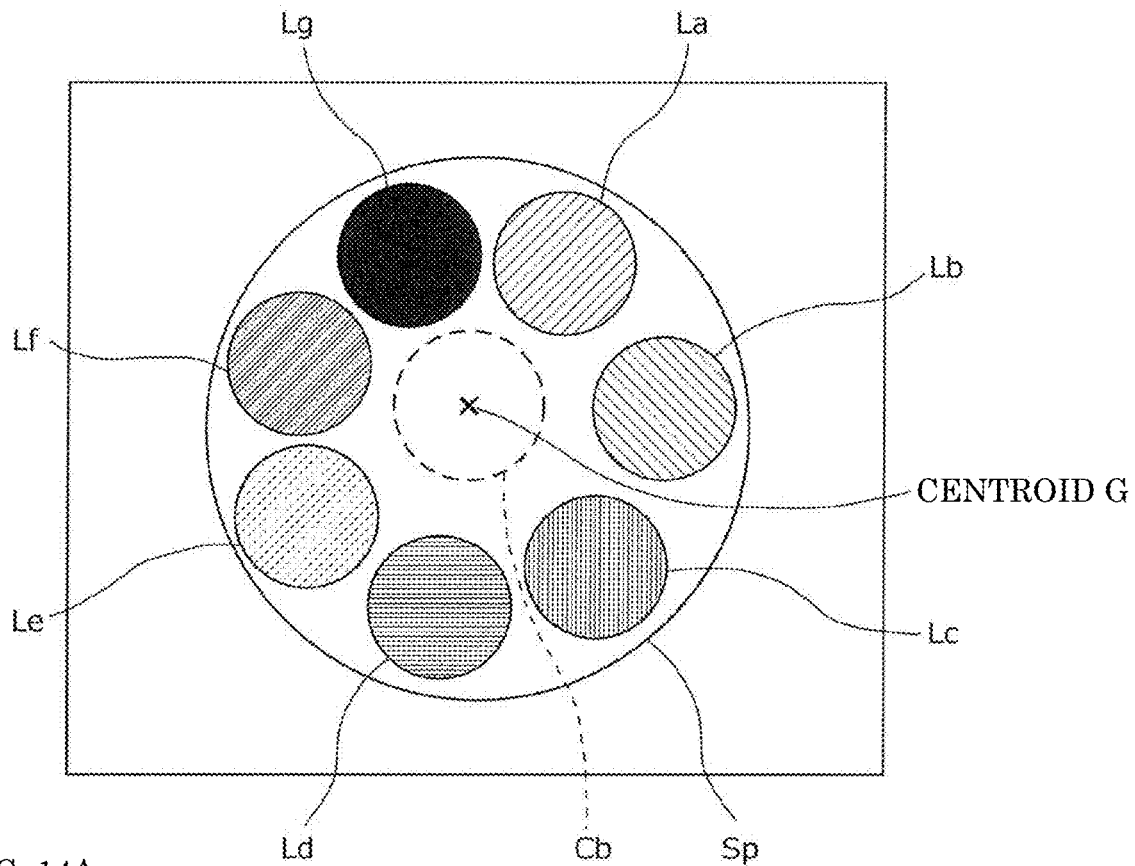
FIG. 13 is a diagram schematically illustrating a method of determining the presence or absence of a cavity part in an image provided by binarizing an in-focus image of the spheroid.
Figure 14A:
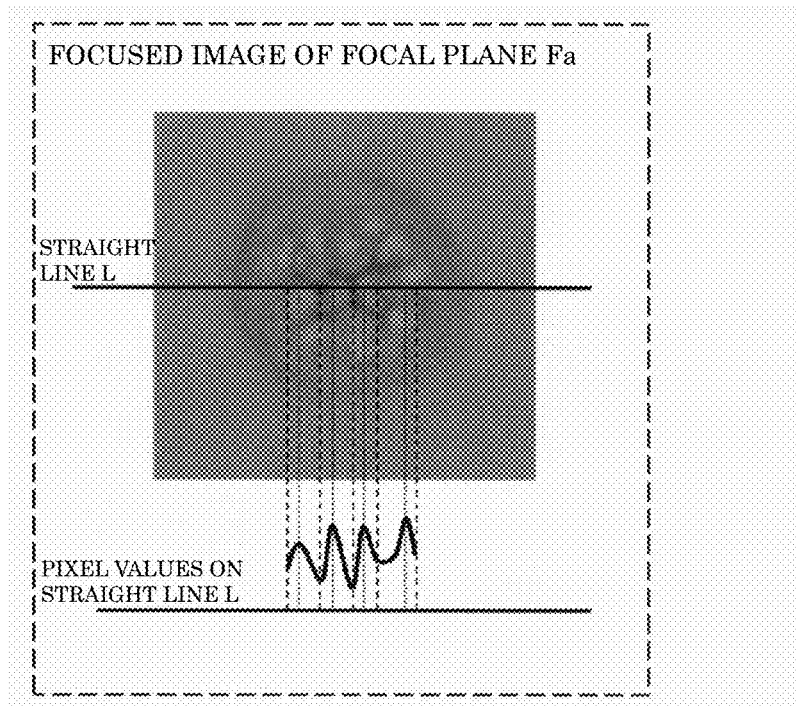
FIG. 14A is a diagram schematically illustrating one example of a relationship between an in-focus image of a spheroid region similar to that of FIG. 9A and a pixel value on the region.
Figure 14B:
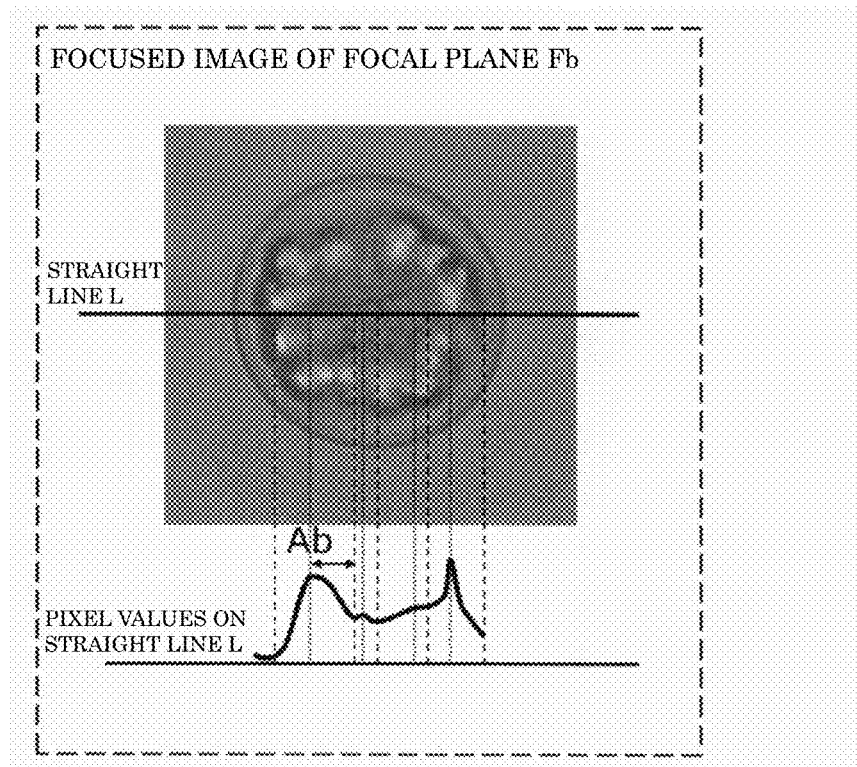
FIG. 14B is a diagram schematically illustrating one example of the relationship between the in-focus image of the spheroid region similar to that of FIG. 9B and the pixel value on the region.
Figure 14C:
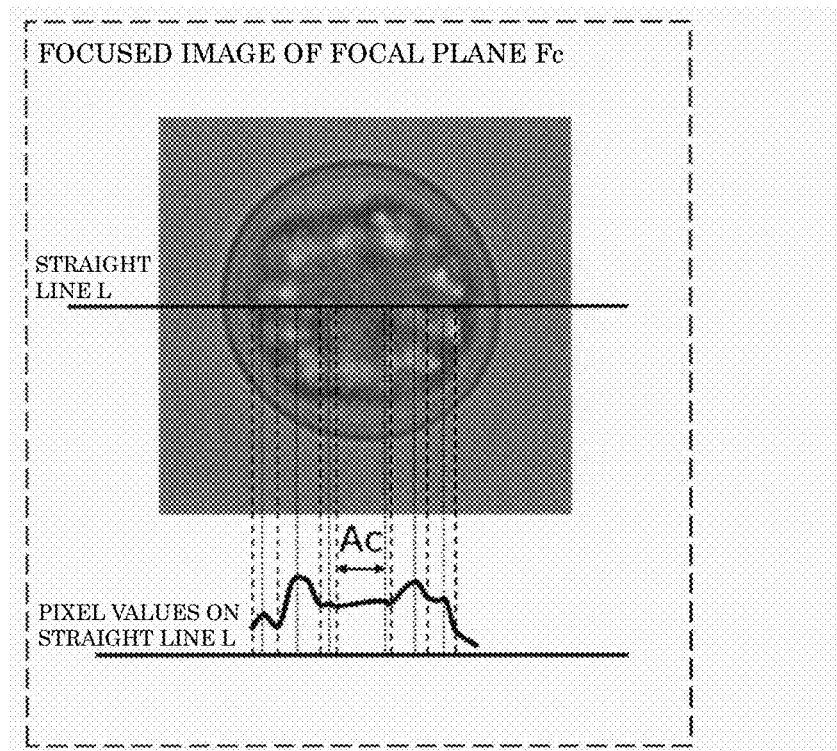
FIG. 14C is a diagram schematically illustrating one example of the relationship between the in-focus image of the spheroid region similar to that of FIG. 9C and the pixel value on the region.
Figure 14D:
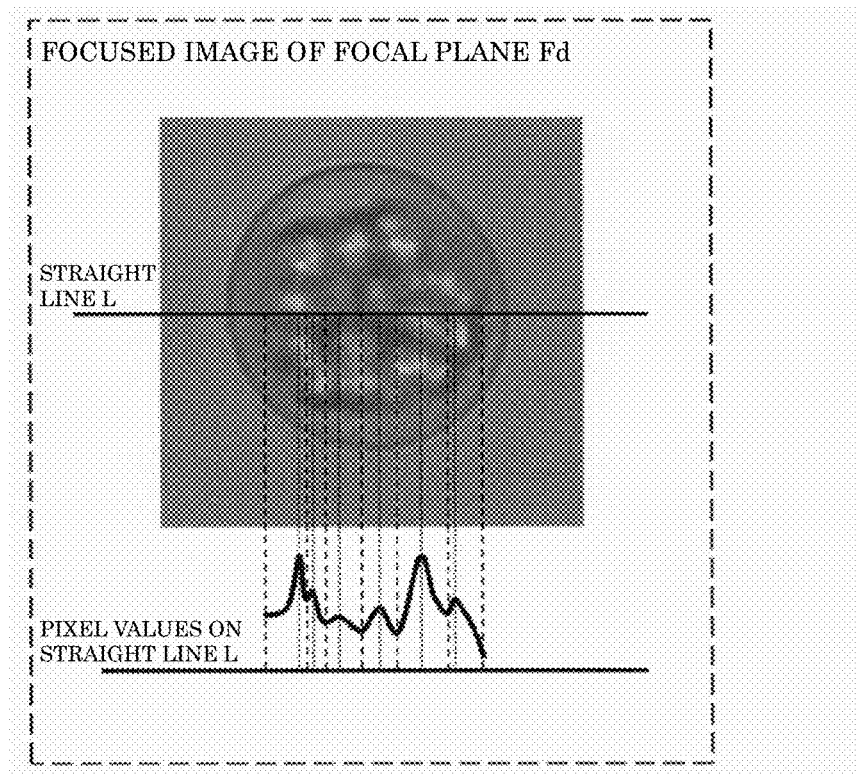
FIG. 14D is a diagram schematically illustrating one example of the relationship between the in-focus image of the spheroid region similar to that of FIG. 9D and the pixel value on the region.

Here, an example of a method for determining the presence or absence of the cavity part from the binarized image as shown in FIGS. 9A to 9D will be described with reference to FIG. 13. FIG. 13 is a diagram schematically illustrating a method of determining the presence or absence of the cavity part in the binarized image of the in-focus image of the spheroid. The discrimination unit 123 labels regions where the pixel value is equal to or greater than the second threshold value in the binarized image of the in-focus image of the spheroid Sp, and determines a first region La to a seventh region Lg, which are seven regions. Further, the discrimination unit 123 determines a centroid G calculated from all of the first region La to the seventh region Lg. For example, the centroid G is a centroid of the seven centroids of the first region La to the seventh region Lg. Then, the discrimination unit 123 forms a circle Cb. The circle Cb has a radius b and has the centroid G as the center thereof. The radius b is, for example, an average of the radii of seven approximate circles when the outer shape of each of the first region La to the seventh region Lg is approximated as a circle. If the circle Cb includes any of the labeled regions, namely, any of the first region La to the seventh region Lg, the discrimination unit 123 determines that the cavity part is absent. On the other hand, if the circle Cb includes none of the first region La to the seventh region Lg, the unlabeled region including the center of gravity G is defined as the cavity part. The unlabeled region may be any one of a region which includes the centroid G and is a region other than the first region La to the seventh region Lg, the circle Cb, or an ellipse which is inscribed in the first region La to the seventh region Lg and includes the centroid G. In the present specification and claims, an "ellipse" includes a circle, an ellipse, or an oval. Also, the circle Cb includes any one of the first region La to the seventh region Lg means that the circle Cb and any one of the first region La to the seventh region Lg form an overlapping region.

In the present embodiment, the discrimination unit 123 determines a labeled region from the binarized image of the in-focus image of the spheroid, and determines a non-labeled region as the cavity part. The cavity part may be determined by another method. For example, the discrimination unit 123 may determine the cavity part based on a change in the pixel values on a line that crosses the spheroid in the in-focus image. For example, FIGS. 14A to 14D schematically show examples of the relationship between the in-focus images of the same spheroid regions as each other on the focal planes Fa to Fd and the pixel values on the regions, similarly to the case in FIGS. 9A to 9D. Specifically, the graphs in the lower parts of FIGS. 14A to 14D schematically show the pixel values of the pixels on a straight line L which passes through the center of the spheroid in the in-focus image in the upper part.

When determining the presence or absence of the cavity part, the discrimination unit 123 determines, for example, the straight line L which passes through the center of the spheroid for each in-focus image as shown in the upper parts of FIGS. 14A to 14D. A distribution of the pixel values of the pixels along the straight line L is provided by the discrimination unit 123 as shown in the lower parts. The position of the straight line L is preferably determined so as to pass through a region where the cavity part is likely to be formed. Since a morula includes the cavity part at the center thereof, the straight line L passes through the center of the spheroid in the present embodiment. Thus, the position of the straight line L can be determined depending on a target cell aggregation of the spheroid.

In the graph of the pixel values on the straight line L as shown in the lower parts of FIGS. 14A to 14D, the discrimination unit 123 calculates the interval between the tops of the peaks and the valleys of the graph, namely, the interval between the peaks and valleys of the pixel values. In FIG. 14A to 14D, the positions of the tops of the valleys of the graph are indicated by broken lines extending from the graph to the in-focus image, and the positions of the tops of the peaks of the graph are indicated by dotted lines extending from the graph to the in-focus image. The broken line indicates the position in the in-focus image corresponding to the peak of the valley of the graph. The dotted line indicates the position in the in-focus image corresponding to the top of the peak of the graph. For example, the discrimination unit 123 calculates eight intervals in the example of FIG. 14A, calculates eight intervals in the example of FIG. 14B, calculates twelve intervals in the example of FIG. 14C, and calculates twelve intervals in the example of FIG. 14D. Furthermore, the discrimination unit 123 calculates the variance of the intervals between the peaks and valleys of the pixel values for each in-focus image.

The discrimination unit 123 determines that the cavity part is absent if the variance of the intervals between the peak and valley of the pixel values is less than a predetermined third threshold value, and determines that the cavity part is present if the variance of the intervals between the peaks and valleys is equal to or greater than the third threshold value. Furthermore, if the cavity part is present, the discrimination unit 123 determines the region which is along the straight line L and has the largest interval between the peaks and valleys as the region of the cavity part. For example, the discrimination unit 123 determines that the cavity part is present in FIGS. 14B and 14C. The discrimination unit 123 determines the region Ab as the cavity part in FIG. 14B, and determines the region Ac as the cavity part in FIG. 14C. In addition, the discrimination unit 123 further determines a plurality of straight lines that pass through the center of the spheroid and are different from the straight line L. The discrimination unit 123 determines the presence or absence of the cavity part on the basis of the distribution of the pixel values along each line, namely, on the basis of the variance of the intervals between the peaks and valleys of the pixel values. The discrimination unit 123 determines the region of the cavity part along the straight lines. The plurality of the straight lines are straight lines each intersecting with the straight line L, and are straight lines provided by rotating the straight line L at the center of the spheroid. The discrimination unit 123 calculates a two-dimensional region of the cavity part along the in-focus image from a one-dimensional region of the cavity part along each of the plurality of the straight lines including the straight line L. For example, the discrimination unit 123 may calculate the two-dimensional region of the cavity part by integrating the one-dimensional region of the cavity part.

The third threshold value is a threshold value for determining the presence of the cavity part in the spheroid. The third threshold value can be determined as various values depending on conditions such as the type and the amount of the cells forming the spheroid and the time point of the culture of the spheroid. Such a third threshold value may be determined depending on the above conditions by a designer, a manufacturer, or a user of the culture state determination device 10, and the determined third threshold value may be input via an input device (not shown) and may be stored in the storage unit 110. For example, the variance of the intervals between the peaks and valleys of the pixel value in a case where the cavity part has a size which is not less than approximately twice as large as the size of the cell is not less than four times as much as the variance of the intervals between the peaks and valleys of the pixel value in a case where the cavity part having a size which is equal to or larger than the size of the cells is absent. If the region that is not less than approximately two times as large as the cell is deemed to be a cavity part, an example of the third threshold value is not less than four times as much as the variance of the intervals between the peaks and valleys of the pixel value if the cavity part having a size equal to or larger than the size of the cell is absent. However, the third threshold value is not limited to such a value, and may be variously determined based on the relationship between the size of the region which is deemed to be the cavity part and the size of the cells.

Next, in the step S1500, the calculation unit 130 determines the number of the first pixel that is a pixel in the region surrounded by the outer shape of the spheroid and the number of the second pixel which is a pixel in the region of the cavity part, for the regions of the outer shape and the cavity part of the spheroid in all the focal planes for each of the regions of the spheroids discriminated in the step S1400. The number of the first pixel is the number of all the pixels included in the outer shape of the spheroid, and the number of the second pixel is the number of all the pixels included in the cavity part. Furthermore, the calculation unit 130 calculates the first total number that is the sum of the number of the first pixels in the region surrounded by the outer shape of the spheroid at all the focal planes of all the regions of the spheroid. Further, the calculation unit 130 calculates the second total number that is the sum of the number of the second pixels in the region of the cavity part of the spheroid at all the focal planes of all the regions of the spheroid. The calculation unit 130 calculates a first ratio of the second total number to the first total number. The first ratio is indicated by the second total number/the first total number. The number of the pixels indicate an area in which the area of one pixel is one unit. The sum of the areas indicated by the number of the pixels on a plurality of parallel focal planes indicates the volume of a three-dimensional region including the pixels in a pseudo manner. Since the spheroid is a mass in which cells are densely aggregated, the ratio of the number of the pixels indicates the ratio of the amount of cells in a pseudo manner in the inside of the outer shape of the spheroid. The amount of the cells may mean the volume of the cells or the number of the cells. Thus, the calculation unit 130 calculates the pseudo cell amount of the spheroid.

Next, in the step S1600, the state determination unit 140 determines the states of the plurality of the cultured spheroids based on the first ratio calculated in the step S1500. If a ratio of the second total number that is the sum of the number of the second pixels included in each of the cavity parts of all the spheroids to the first total number that is the sum of the number of the first pixels included in each of the outer shapes of all the spheroids is large, the culture state is allowed to be determined to be bad. Specifically, the state determination unit 140 determines that the culture state is good, if the first ratio is lower than a predetermined determination reference value. On the other hand, the state determination unit 140 determines that the culture state is bad, if the first ratio is equal to or higher than the determination reference value. In the present embodiment, the determination reference value is 0.3. If the second total number is 30% or more of the first total number, the state determination unit 140 determines that the culture state is bad and determines to discard all the plurality of the spheroids in the culture vessel 1. If the second total number is less than 30% of the first total number, the state determination unit 140 determines that the culture state is good, and determines to be used for the processing after the culture. As described above, the state determination unit 140 determines a state in which a plurality of spheroids contain more cells as a good culture state. In other words, a good culture state is a culture state in which there are more cells that can be used for the processing after the culture, and an efficient processing after the culture is possible.

Next, in the step S1700, the display unit 150 shows the determination result of the step S1600 to the user. At this time, the display unit 150 shows the output of images, characters, sounds, and the like via a display and/or a speaker.

1-3. Imaging Processing

Figure 15:
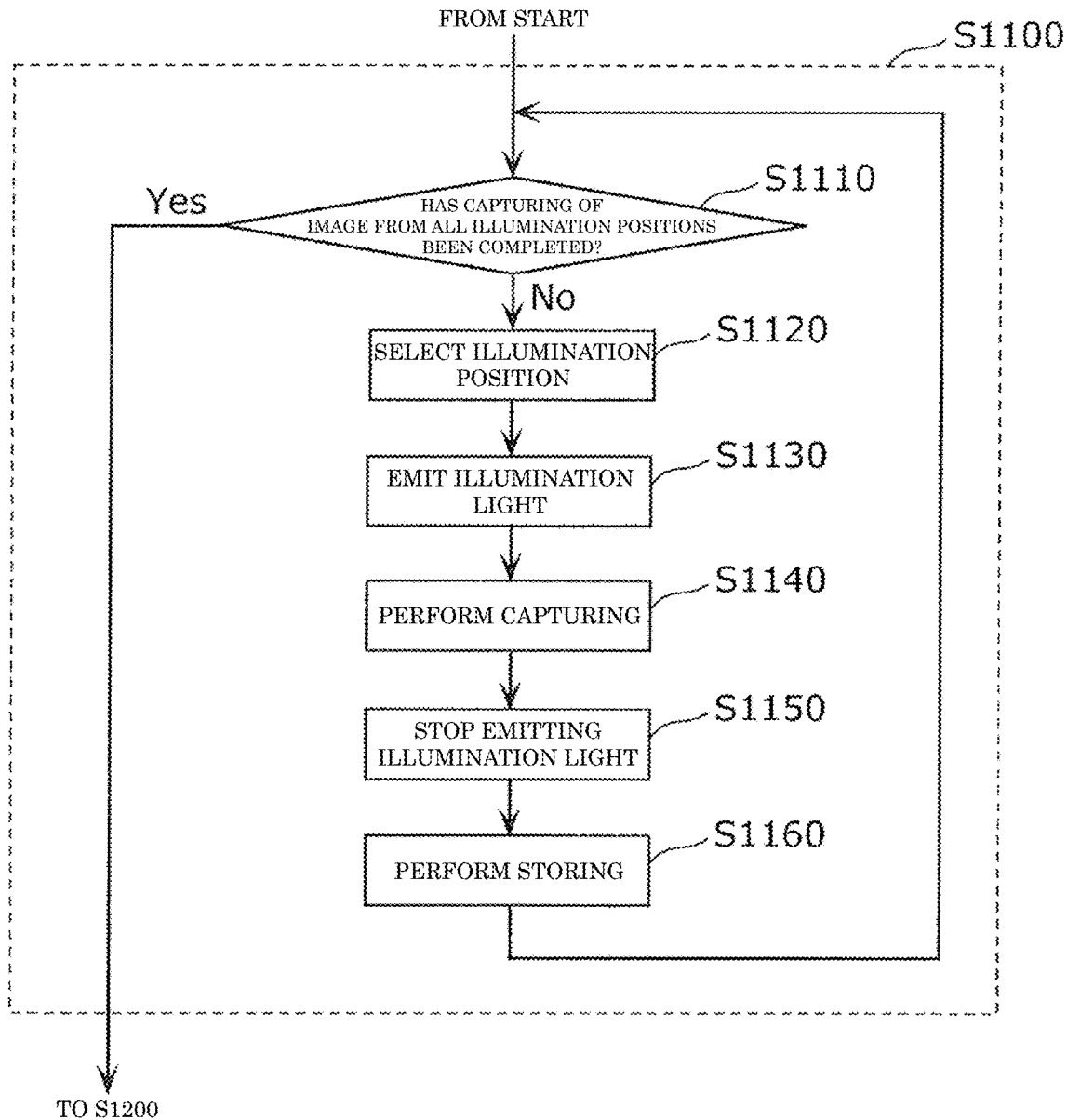
FIG. 15 is a flowchart illustrating one example of operation of the imaging device according to the first embodiment.

Details of the operation of the imaging device 100 in the step S1100 will be described with reference to FIG. 15. FIG. 15 is a flowchart illustrating one example of the operation of the imaging device 100.

In the step S1110, the imaging control unit 103 determines whether or not capturing of the image of the plurality of the spheroids illuminated from the position of each of the illuminators 101 is completed with reference to, for example, a list of positions of the predetermined plurality of the illuminators 101 stored in the storage unit 110 or a list of positions of the plurality of the illuminators 101 designated by an external input which is not shown (hereinafter, each of the lists is referred to as "illumination position list").

Here, if the capturing of the image with illumination from all illumination positions included in the illumination position list has been completed (Yes in step S1110), the imaging control unit 103 proceeds to the step S1200. On the other hand, if the capturing of the images with illumination from any illumination positions in the illumination position list has not been completed (No in step S1110), the imaging control unit 103 proceeds to the step S1120.

Next, in the step S1120, the imaging control unit 103 selects an illumination position that has not yet been illuminated from among the plurality of the illumination positions included in the illumination position list, and outputs a control signal to the illuminator 101 at the selected illumination position. In the illumination position list, each illumination position is indicated by, for example, a number assigned to each illumination position. Alternatively, each illumination position is indicated by, for example, the coordinate value of the three-dimensional coordinate space defined by the x-axis and y-axis which are included in the light receiving surface of the image sensor 102, and the z-axis perpendicular to the light receiving surface. The selection of the illumination position is performed, for example, in ascending order of the list.

Next, in the step S1130, the illuminator 101 starts illumination of the plurality of the spheroids in the culture vessel 1 on the image sensor 102 in accordance with the control signal output from the imaging control unit 103 in the step S1120. In other words, the illuminator 101 at the illumination position selected in the step S1120 starts illumination of light.

Next, in the step S1140, while the plurality of the spheroids are illuminated by the illuminator 101, the imaging control unit 103 causes the image sensor 102 to acquire a captured image formed by the light emitted from the illuminator 101. The captured image includes an image formed by the light transmitted through the spheroids.

Next, in the step S1150, the imaging control unit 103 outputs a control signal to the illuminators 101, and stops the illumination on the spheroids. The stop of the illumination does not have to be performed in accordance with a control signal from the imaging control unit 103. For example, the illuminator 101 may measure the time length from the start of the illumination and actively stop the illumination, when the measured time length exceeds a predetermined time length. Alternatively, after the image sensor 102 finishes acquiring the captured image in the step S1140, the image sensor 102 may output a control signal to stop the illumination to the illuminator 101.

Next, in the step S1160, the imaging control unit 103 stores the captured image acquired in the step S1140 and the position information of the illuminator 101 used in the step S1130 in the storage unit 110 in association with each other.

The imaging control unit 103 returns to the step S1110 after the processing of the step S1160.

The imaging control unit 103 repeats the processing from the step S1110 to the step S1160 to sequentially irradiate the spheroids with light from the illuminators 101 at all the illumination positions included in the illumination position list. In this way, the imaging control unit 103 acquires the captured image every time when the spheroids are irradiated with light.

1-4. Refocusing Processing

Figure 16:
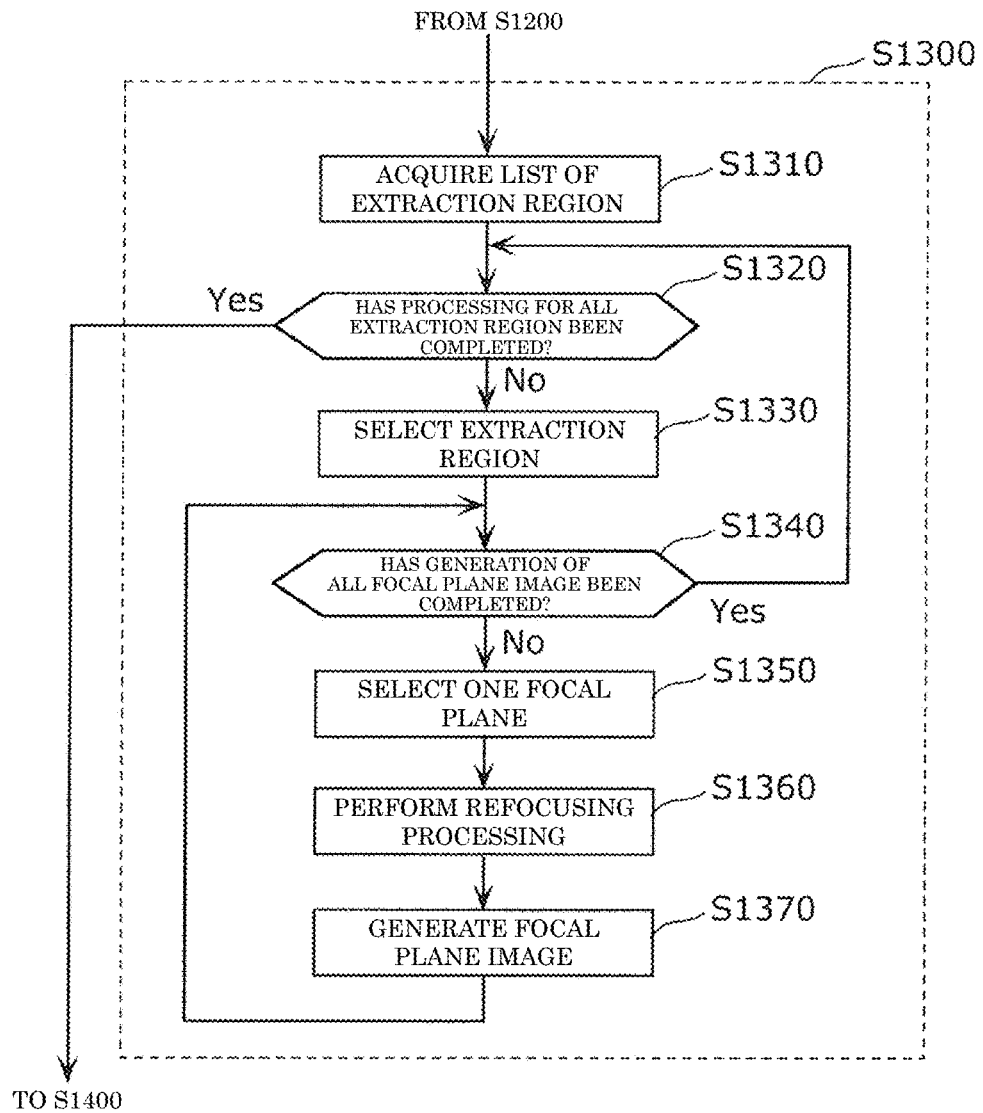
FIG. 16 is a flowchart illustrating one example of operation of the internal image generation unit according to the first embodiment.

Details of the operation of the refocusing unit 1221 in the step S1300 will be described with reference to FIG. 16. FIG. 16 is a flowchart showing one example of the operation of the refocusing unit 1221 according to the first embodiment.

In the step S1310 which follows the step S1200, the refocusing unit 1221 acquires a list of one or more extraction regions determined using the reference captured image in the step S1200, namely, a list of the regions each including the image of the spheroid from the storage unit 110. In the following description, the extraction region and the region including the image of the spheroid are referred to as a "spheroid region". The list is, for example, a list as shown in FIG. 5.

Next, in the step S1320, the refocusing unit 1221 refers to the list of the spheroid regions acquired in the step S1310, and determines whether or not the refocusing processing for all the spheroid regions has been completed. The completion of the refocusing processing for all the spheroid regions means the completion of a series of the processing in the steps S1320 to S1370. In other words, the completion of the refocusing processing for all the spheroid regions means the processing of generating the in-focus images at all the predetermined focal planes using the plurality of the captured images is completed for each spheroid region.

If the refocusing processing has been completed for all the spheroid regions included in the list of the spheroid regions (Yes in step S1320), the refocusing unit 1221 proceeds to the step S1400. On the other hand, if the refocusing processing for any spheroid region in the list of the spheroid regions has not been completed (No in step S1320), the refocusing unit 1221 proceeds to the step S1330.

Next, in the step S1330, the refocusing unit 1221 selects one spheroid region that has not been refocused, namely, an extraction region, from the list of the spheroid regions acquired in the step S1310. The refocusing processing of the spheroid region is a series of processing in the steps S1340 to S1370.

Next, in the step S1340, the refocusing unit 1221 determines whether or not the generation of the in-focus images at all focal planes has been completed for the selected spheroid region with reference to the focal plane table 1222 that has stored information on the plurality of the predetermined focal planes and the list of the spheroid regions acquired in the step S1310.

If the generation of the in-focus images on all focal planes stored in the focal plane table 1222 has been completed (Yes in step S1340), the refocusing unit 1221 returns to step S1320. On the other hand, if the generation of the in-focus images on all the focal planes stored in the focal plane table 1222 has not been completed (No in step S1340), the refocusing unit 1221 proceeds to the step S1350.

Next, in the step S1350, the refocusing unit 1221 selects one focal plane that has not yet generated a corresponding in-focus image from the focal planes stored in the focal plane table 1222.

Next, in the step S1360, the refocusing unit 1221 performs refocusing processing on the focal plane selected in the step S1350 using the plurality of the captured images acquired in the step S1100 for the spheroid region selected in the step S1330, and generates an in-focus image of the spheroid region on the focal plane.

For example, the refocusing unit 1221 performs the refocusing processing in the same manner as in Patent Literature 4. The in-focus image includes a plurality of focused pixels. The plurality of the focused pixels included in the in-focus image correspond one-to-one to a plurality of points on the focal plane. According to the same method as in Patent Literature 4, the refocusing unit 1221 calculates a point corresponding to the spheroid region on the focal plane, and further calculates the pixel coordinates of the focused pixel corresponding to the point. Further, the refocusing unit 1221 calculates the light arrival position on the light receiving surface of the image sensor 102 when light emitted from the plurality of the different illumination positions passes through the position of the focused pixel and reaches the light receiving surface of the image sensor 102. The refocusing unit 1221 calculates the position of the point where the illumination light that has passed through the position of the focused pixel reaches the image sensor 102 for each of the plurality of the different illumination positions for one focused pixel. The refocusing unit 1221 acquires pixel values acquired by the image sensor 102 at the position of the arrival point from the plurality of the captured images. Specifically, the refocusing unit 1221 acquires the pixel value at the pixel coordinates of the arrival point of the light from the illumination position in the captured image corresponding to each illumination position. Further, the refocusing unit 1221 calculates the pixel value of the focused pixel by adding the pixel values at the arrival points on the image sensor 102 acquired for all the illumination positions with respect to the focused pixel. In other words, the refocusing unit 1221 calculates the pixel value of the focused pixel by adding the pixel value at the pixel coordinate of the arrival point acquired in each captured image corresponding to all the illumination positions. Further, the refocusing unit 1221 performs the above calculation for all focused pixels on the focal plane on which an in-focus image is to be generated, namely, for all focused pixels corresponding to the spheroid region.

Next, in the step S1370, the image generation unit 1223 generates in-focus image data of the spheroid region on the basis of the pixel value for each focused pixel on the in-focus image generated in the step S1360, namely, generates the image data of the spheroid region in the focal plane corresponding to the in-focus image. Further, the image generation unit 1223 stores the in-focus image data of the spheroid region in the storage unit 110 in association with the information on the spheroid region and the position information on the focal plane corresponding to the in-focus image. The image generating unit 1223 returns to the step S1340 after the step S1370 is completed.

As described above, by repeating the processing from the step S1340 to the step S1370, in-focus images on all focal planes stored in the focal plane table 1222 are generated for the spheroid region selected in the step S1330.

Further, by repeating the processing from the step S1320 to the step S1370, the in-focus images on all focal planes stored in the focal plane table 1222 are generated for all the spheroid regions extracted in the step S1200.

Figure 17:
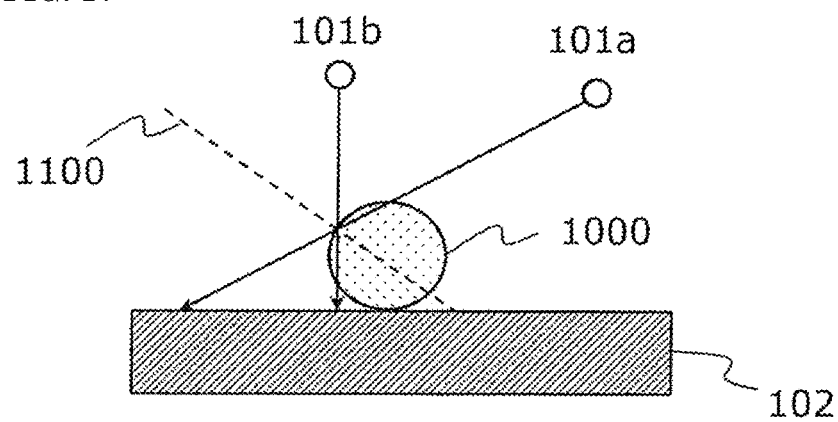
FIG. 17 is a schematic diagram illustrating a specific example of a refocusing processing according to the first embodiment.

Here, a specific example of the calculation method of the refocusing processing will be described with reference to FIGS. 17-20. In this embodiment, the focal plane is a plane parallel to the light receiving surface of the image sensor 102. In the following, a case where the focal plane intersects the light receiving surface of the image sensor 102 will be described. The specific calculation method is the same as one another in all cases. For example, FIG. 17 illustrates one example of a positional relationship among the plurality of the illuminators 101 of the imaging device 100, a spheroid 1000, and the image sensor 102. FIG. 17 shows one example of a cross-sectional view of the image sensor 102 and the spheroid 1000 in a plane perpendicular to the light receiving surface of the image sensor 102. The spheroid 1000 is located between the illuminators 101a and 101b and the image sensor 102 and is located on the image sensor 102. A focal plane 1100 for generating an in-focus image passes through the spheroid 1000 and intersects the light receiving surface of the image sensor 102.

Figure 18:
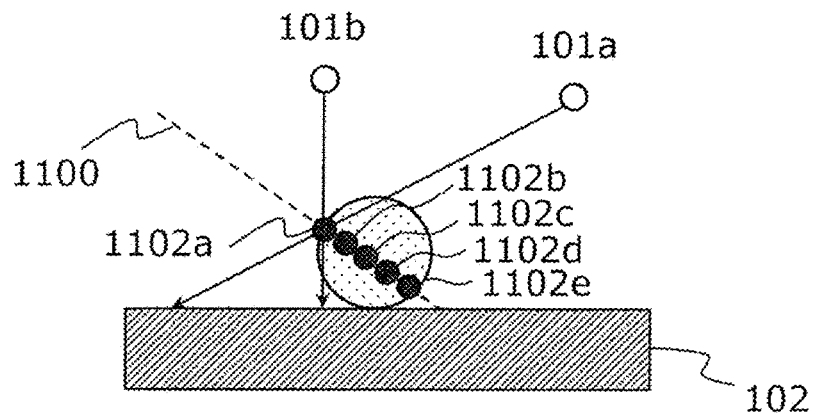
FIG. 18 is a schematic diagram illustrating a specific example of the refocusing processing according to the first embodiment.
Figure 19:
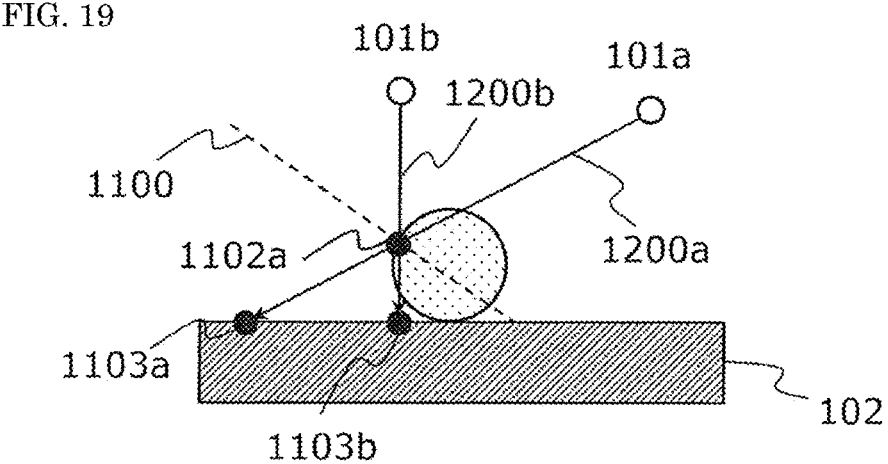
FIG. 19 is a schematic diagram illustrating a specific example of the refocusing processing according to the first embodiment.

FIG. 18 shows one example of a plurality of points 1102a to 1102e on the focal plane 1100 corresponding to a plurality of focused pixels included in the in-focus image, similarly to the case of FIG. 17. A method for generating a focused pixel corresponding to the point 1102a among the plurality of the points 1102a to 1102e will be described. Since the method for generating focused pixels corresponding to other points is the same as that of the point 1102a, the description thereof is omitted. FIG. 19 shows an example in which light emitted from each of the illuminators 101a and 101b passes through the point 1102a on the focal plane and is received by the image sensor 102.

The light emitted from the illuminators 101a and passed through the point 1102a travels on a straight line 1200a passing through the position of the illuminator 101a and the point 1102a, and reaches an intersection 1103a between the straight line 1200a and the light receiving surface of the image sensor 102. The luminance value of the light reaching the intersection 1103a from the illuminators 101a is included in the captured image of the image sensor 102 when the illuminator 101a is illuminated. In the captured image, a pixel at a position corresponding to the intersection 1103a includes an image at the point 1102a on the focal plane 1100, namely, a luminance value. The position of the intersection 1103a can be calculated from the position of the illuminator 101a and the position of the point 1102a.

The light emitted from the illuminator 101b and passed through the point 1102a travels on a straight line 1200b passing through the position of the illuminators 101b and the point 1102a, and reaches an intersection 1103b between the straight line 1200b and the light receiving surface of the image sensor 102. The luminance value of the light reaching the intersection 1103b from the illuminators 101b is included in the captured image of the image sensor 102 when the illuminator 101b is illuminated. In the captured image, a pixel at a position corresponding to the intersection 1103b includes an image at the point 1102a on the focal plane 1100, namely, a luminance value. The position of the intersection 1103b can be calculated from the position of the illuminator 101b and the position of the point 1102a.

By adding the luminance value of the image at the intersection 1103a and the luminance value of the image at the intersection 1103b, a plurality of images formed by light from a plurality of directions are superimposed on the focused pixel at the point 1102a on the focal plane 1100. A focused pixel at the point 1102a is generated by superimposing a plurality of images formed by light transmitted from all the illuminators 101 through the point 1102a. In this way, by using the luminance values of each of the sensor pixels in a condition where in which the position of the illuminators 101, the position of the focused pixel, and the position of the sensor pixel of the image sensor 102 are aligned on a straight line, the luminance value of the focused pixel is calculated.

Figure 20:
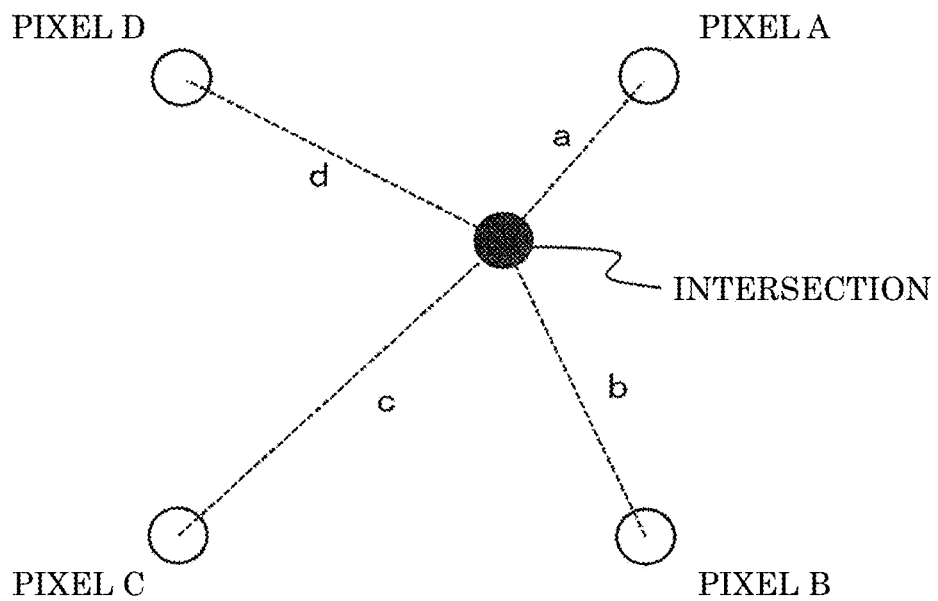
FIG. 20 is a schematic diagram illustrating a specific example of the refocusing processing according to the first embodiment.

If the position of the intersection in the captured image matches the position of the pixel in the captured image, the luminance value of the pixel may indicate the luminance value of the intersection. If the position of the intersection in the captured image is an intermediate position between the plurality of pixels in the captured image, the luminance value of the intersection in the captured image may be calculated by performing an interpolation processing using the luminance values of the plurality of pixels adjacent to the position of the intersection. Specifically, for example, as shown in FIG. 20 and the following formula 1, for a plurality of pixels (for example, four pixels) adjacent to the intersection, the ratio of a reference distance to the distance between each pixel and the intersection is multiplied by the luminance value of each pixel, and added. In this way, the luminance value of the intersection in the captured image can be provided. In FIG. 20, the distances between the four pixels A to D adjacent to the intersection and the intersection are represented as a, b, c, and d, respectively. In this case, the luminance value Lt of the intersection can be calculated in accordance with the following formula 1.

$$Lt = \frac{1}{4}\left(\frac{La}{a} + \frac{Lb}{b} + \frac{Lc}{c} + \frac{Ld}{d}\right) \times S \qquad \text{[Formula 1]}$$

where, La, Lb, Lc, and Ld represent the luminance values of the pixel A, the pixel B, the pixel C, and the pixel D, respectively. S represents a reference distance. For example, S may be an average of the distance between the intersection and each pixel as shown in the following formula 2.

$$S = \frac{a+b+c+d}{4} \qquad \text{[Formula 2]}$$

1-5. Effect

As described above, the culture state determination device 10 according to the first embodiment performs the refocusing processing using the plurality of the captured images each having different illumination position from one another at the time when the images are captured to generate the in-focus images of the plurality of the spheroids at each of the plurality of the parallel focal planes and to discriminate the outer shape of the spheroid from the cavity part of the inside of the spheroid on each in-focus image. Furthermore, the culture state determination device 10 calculates the number of the first pixels forming the inner region of the outer shape of each spheroid and the number of the second pixels forming the cavity part on all focal planes, and calculates the volume of the spheroid and the volume of the cavity part each having the pixel as a unit. Thereby, the amount of the cells forming the spheroid is allowed to be calculated in a pseudo manner. For a culture vessel containing a plurality of spheroids, the state where the first ratio of the volume of the cavity part to the volume of the spheroids in the entire culture vessel is small is a state where the amount of the cells provided as a result of culture is relatively large. Such a state can be determined as the state where the culture state is good. Since the culture state determination device 10 can determine the quality of the culture state based on not the quality of the culture state of individual spheroid but the efficiency of the culture in the entire culture vessel, the efficiency of acquiring cells that can be used for the processing after the culturing can be improved, and the amount of the provided cells can be increased. As just described, the culture state determination device 10 simultaneously captures the images of the plurality of the spheroids in the same culture vessel, and evaluates the state of the inside of all the spheroids. In this way, the culture state determination device 10 determines the quality of the culture state of the entire spheroids contained in the same culture vessel, and allows usable spheroids to be selected.

In the culture state determination device 10 according to the first embodiment, in the step S1200, the region extraction unit 121 extracts the region in which a spheroid has been photographed from the captured image, and, in the step S1300, the internal image generation unit 122 performs the refocusing processing for each extracted region to generate an in-focus image at each focal plane. However, the present disclosure is not limited to this. The culture state determination device 10 does not perform the region extraction in the step S1200, and the internal image generation unit 122 may set the range of the light receiving surface of the image sensor 102 to be the xy plane direction in the step S1300, for example, and may perform the refocusing processing for all the pixels in the three-dimensional space in which the z axis is orthogonal to the xy plane. In this case, the discrimination unit 123 extracts the outer shape of the plurality of the spheroids in the three-dimensional space, and discriminates the cavity part in the outer shape of each of the spheroids. Further, the calculation unit 130 calculates the number of the first pixels included in the outer shape of each of the plurality of the spheroids and the number of the second pixels included in the cavity part of each of the spheroids. Note that in the refocusing processing for all the pixels in the three-dimensional space, the internal image generation unit 122 may generate the in-focus images on all focal planes. The discrimination unit 123 may extract the outer shape of each of the spheroids and the cavity part of each of the spheroids in the in-focus image of each focal plane.

Second Embodiment

A culture state determination device 20 according to the second embodiment will be described. The culture state determination device 20 according to the second embodiment calculates the size of the plurality of the spheroid regions in the reference captured image. Furthermore, if the distribution in the size of the plurality of the spheroid regions is large, the culture state determination device determines that the culture state is bad. Hereinafter, the second embodiment will be described with a focus on differences from the first embodiment.

Figure 21:
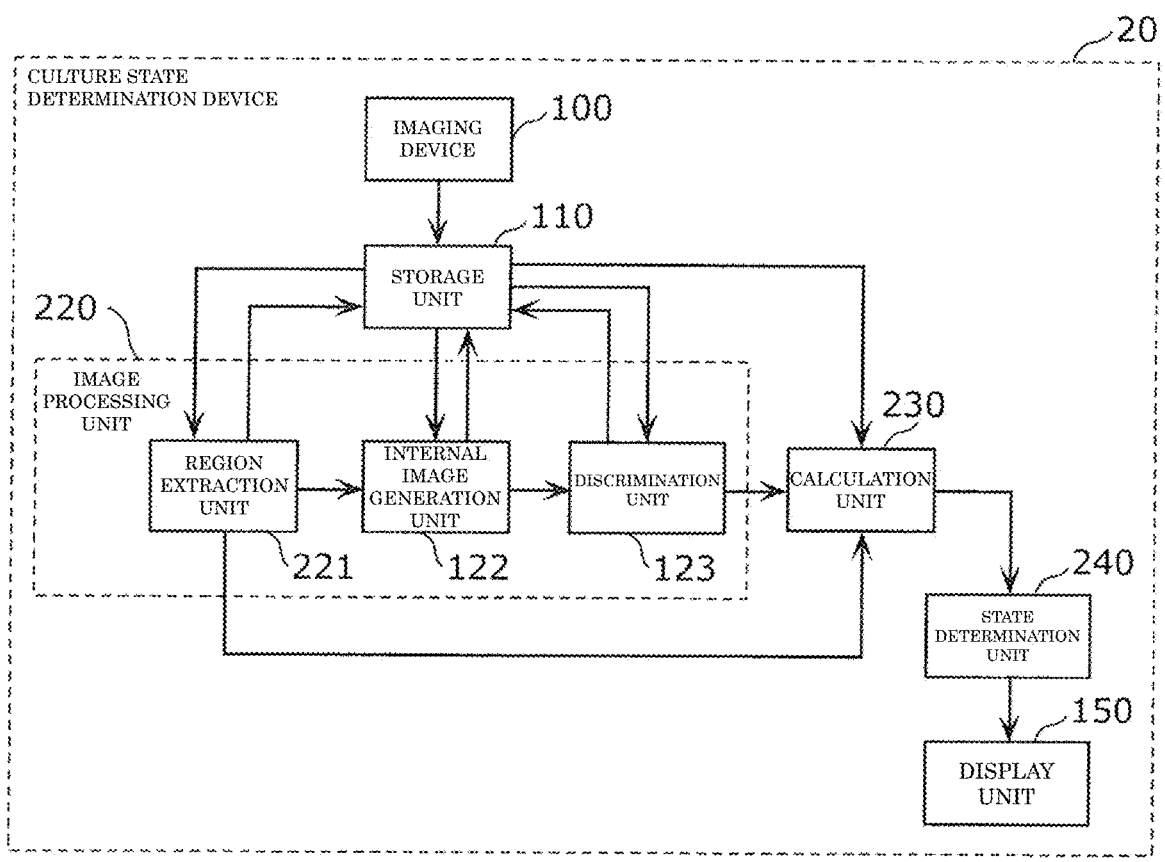
FIG. 21 is a block diagram illustrating one example of a functional configuration of a culture state determination device according to a second embodiment.

2-1. Configuration of Culture State Determination Device According to Second Embodiment FIG. 21 is a block diagram illustrating one example of a functional configuration of the culture state determination device 20 according to the second embodiment. In FIG. 21, substantially the same components as those in FIG. 1 are denoted by the same reference numerals, and description thereof will be omitted appropriately. As illustrated in FIG. 21, the culture state determination device 20 comprises the imaging device 100, the storage unit 110, an image processing unit 220, a calculation unit 230, a state determination unit 240, and the display unit 150. Further, the image processing unit 220 comprises a region extraction unit 221, the internal image generation unit 122, and the discrimination unit 123. The configurations of the imaging device 100 and the storage unit 110 are the same as those in the first embodiment.

Similarly to the region extraction unit 221 according to the first embodiment, the region extraction unit 221 of the image processing unit 220 determines a reference captured image from a plurality of the captured images, and extracts regions where a spheroid image is present, namely, the spheroid regions, from the reference captured image. Furthermore, the region extraction unit 221 assigns an ID to each of the extracted spheroid regions. The region extraction unit 221 stores information such as the ID and position of each extracted spheroid region in the storage unit 110 in association with the reference captured image from which the spheroid regions have been extracted.

Figure 22:
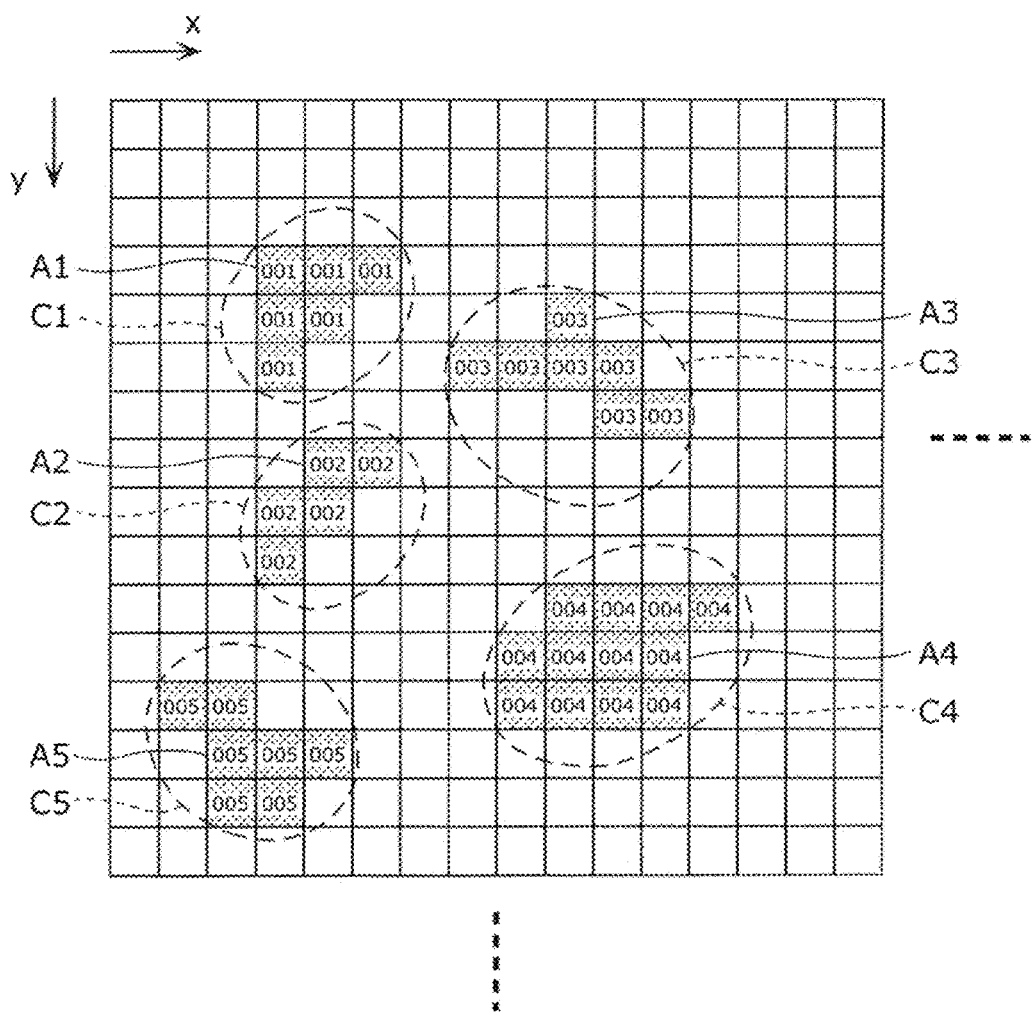
FIG. 22 is a schematic diagram illustrating one example of the spheroid region extracted from a reference captured image.

In the present embodiment, the region extraction unit 221 calculates pixel coordinates of the pixels forming the spheroid regions on the reference captured image as information on the spheroid regions. Furthermore, the region extraction unit 221 assigns, to the calculated pixels, the same ID as the spheroid regions formed by the pixels. For example, FIG. 22 schematically illustrates one example of spheroid regions extracted from the reference captured image. The squares in FIG. 22 schematically show a part of the pixels of the reference captured image. The region extraction unit 221 extracts five spheroid regions A1 to A5 in the part of the reference captured image shown in FIG. 22, and assigns 001 to 005 as IDs to the five spheroid regions A1 to A5, respectively. Further, the same IDs 001 to 005 as those of the spheroid regions are assigned to the pixels included in the spheroid regions A1 to A5 as labels. The region extraction unit 221 stores the pixel coordinates on the reference captured image in the pixels included in each of the spheroid areas A1 to A5 and the ID001 to 005 of the pixels in the storage unit 110 in association with each other. In the example of FIG. 23, the top left vertex on the drawing, which is one of the vertices of the reference captured image, is defined as the origin of the pixel coordinates, the x coordinate is defined from the origin to the left, and the y coordinate is defined from the origin to the bottom.

The region extraction unit 221 may incorporate information on the pixel coordinates and ID of the spheroid region into a file of the reference captured image as shown in FIG. 22. In this case, the information on the spheroid region is stored in the storage unit 110 as an image file. Alternatively, the region extraction unit 221 may generate data of the pixel coordinates and the ID of the spheroid region and store the data in the storage unit 110 so as to form a table as shown in FIG. 23. FIG. 23 shows one example of the content stored in the storage unit 110 for the information on the spheroid region.

The configurations of the internal image generation unit 122 and the discrimination unit 123 of the image processing unit 220 are the same as those in the first embodiment.

The calculation unit 230 extracts the information on the spheroid regions extracted by the region extraction unit 221 and stored in the storage unit 110, and calculates the size of each spheroid region. Specifically, the calculation unit 230 sets, for each spheroid region stored as a continuous pixel region, a minimum ellipse including the spheroid region on the image coordinates of the reference captured image, and calculates the major axis and minor axis of the ellipse. Note that the image for setting the ellipse may be a captured image other than the reference captured image. For example, as shown in FIG. 22, the calculation unit 230 sets the minimum ellipses C1 to C5 circumscribing the spheroid regions A1 to A5, respectively, and calculates the major axis and minor axis of each of the ellipses C1 to C5. The ellipse may include a circle and an ellipse. Furthermore, the calculation unit 230 calculates the sum of the lengths of the major axis and minor axis of each ellipse, and determines the sum as the size of the spheroid. The calculation unit 230 may calculate a size distribution based on the ellipses of all spheroid regions, for example, a statistic such as a maximum value, a minimum value, a median value, an average, and a variance. Furthermore, the calculation unit 230 may create a histogram indicating the distribution of the size of all spheroid regions. The size of the spheroid region is not limited to the sum of the lengths of the major axis and minor axis of the smallest ellipse including the spheroid region. For example, the size of the spheroid region may be the area of the region, the total area of the pixels included in the region, namely, the number of the pixels, the area of the smallest polygon including the spheroid region, or the sum of the lengths of diagonals of the smallest polygon.

Further, the calculation unit 230 calculates the first ratio between the first total number and the second total number that are the total number of the first and second pixels in the entire spheroid region, respectively, on the basis of the number of the first pixels in each spheroid and the number of the second pixels in the cavity part in the spheroid, both of which have been discriminated by the discrimination unit 123

The state determination part 240 determines the quality of the culture state using the information on the distribution of the size of the spheroids calculated by the calculation unit 230. The state determination part 240 determines that the culture state is bad, if the distribution of the size of the spheroids is large, and determines that the culture state is good, if the distribution of the size of the spheroid is small. The state determination part 240 determines the distributions by applying a reference of the distribution, for example, a predetermined fourth threshold value, to the distribution of the size of the spheroids.

The fourth threshold value is a threshold value indicating that the culture state is bad if the distribution of the size of the spheroids is greater than or equal to the fourth threshold value, and that the culture state is not bad if the distribution of the size of the spheroids is less than the fourth threshold value. The fourth threshold value can be determined to have various values depending on conditions such as the kind and the quantity of cells forming the spheroid, the time of the culture of the spheroid, the state of the required quality of the spheroid, and the use of the spheroid. For example, the fourth threshold value may be determined on the basis of a statistical result of a relationship between the distribution of the sizes of the plurality of the spheroids detected by experiments and the culture state of the spheroids. Such a fourth threshold value may be determined depending on the above conditions by a designer, a manufacturer, or a user of the culture state determination device 10, and the determined fourth threshold value may be input via an input device (not shown) and stored in the storage unit 110.

Furthermore, the state determination part 240 compares the first ratio between the first total number and the second total number to a predetermined determination reference value, and determines that the culture state is good if the first ratio is lower than the determination reference value, and that the culture state is bad if the first ratio is greater than or equal to the determination reference value.

The display unit 150 shows the distribution of the size of the spheroids calculated by the calculation unit 230 and the result determined by the state determination part 240. The display unit 150 may display the display content on a display, for example, as a graph, characters, symbols, images, etc., may be displayed as a sound or an acoustic signal on a speaker, or may be displayed in another display method.

Figure 24:
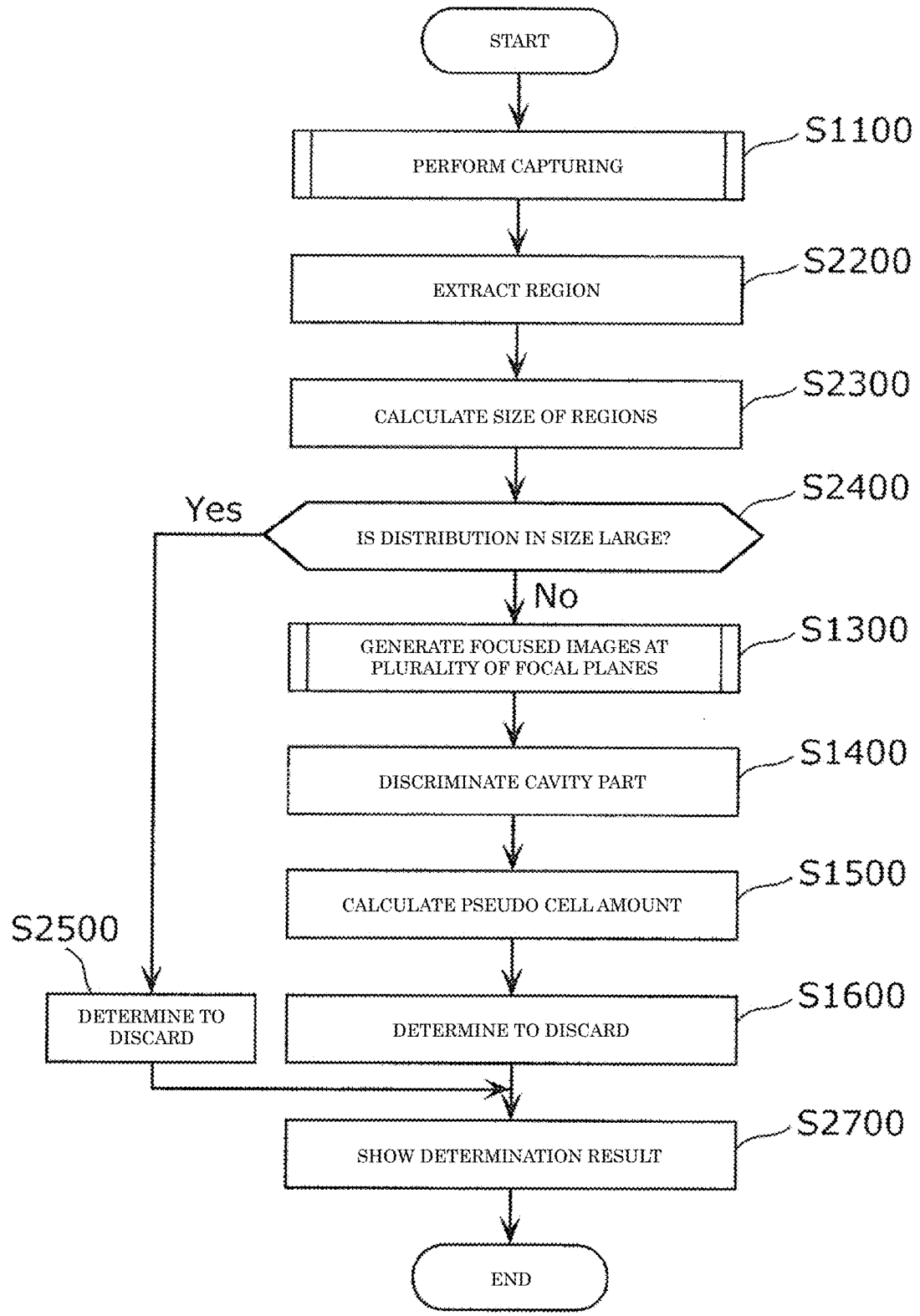
FIG. 24 is a flowchart illustrating one example of operation of the culture state determination device according to the second embodiment.

2-2, Operation of Culture State Determination Device According to Second Embodiment The operation of the culture state determination device 20 according to the second embodiment will be described with reference to FIG. 24. FIG. 24 is a flowchart showing one example of the operation of the culture state determination device 20 according to the second embodiment. In FIG. 24, substantially the same steps as those in FIG. 11 are denoted by the same reference numerals, and description thereof will be omitted as appropriate.

First, in the step S1100, the imaging device 100 performs the same processing as the step S1100 of the first embodiment. Next, in the step S2200, the region extraction unit 221 of the image processing unit 220 determines a reference captured image from the captured image acquired in the step S1100, and extracts a spheroid region from the reference captured image. For each of the one or more spheroid regions extracted from the reference captured image, the region extraction unit 221 stores pixel coordinates on the reference captured image of the pixels included in the region and an ID of the region that is the label of the pixel in association each other in the storage unit 110.

Next, in the step S2300, the calculation unit 230 determines the size of each of the spheroid regions on the reference captured image on the basis of the information on the pixel coordinates and IDs of the pixels included in the spheroid regions extracted in the step S2200 and stored in the storage unit 110. Furthermore, the calculation unit 230 stores information on the size of each spheroid region in the storage unit 110 in association with the ID of the region. In the present embodiment, the size of the spheroid region is, for example, the sum of the lengths of the major axis and minor axis of the smallest ellipse including the region. In the present embodiment, the index of the size of the spheroid region is the sum of the lengths of the major axis and minor axis of the ellipse; however, the index may be another index such as length of diagonal in a polygon such as the smallest rectangular polygon including the spheroid region, the sum of the diagonals of the polygon, the number of the pixels included in the spheroid area, or the square root thereof. The calculation unit 230 may create a histogram indicating the distribution of the size of all spheroid regions based on the size of each spheroid region and store the histogram in the storage unit 110. The calculation unit 230 may calculate a statistic amount of the size of the spheroids region based on the size of each spheroid region and store the statistic amount in the storage unit 110.

Next, in the step S2400, based on the index of the size of the spheroid region calculated in the step S2300, namely, the sum of the lengths of the major axis and minor axis of the smallest ellipse including the spheroid region, the state determination part 240 determines whether or not the distribution of the size of all the spheroid regions extracted in the step S2200 is large. At this time, the state determination part 240 determines whether or not the distribution of the size of all spheroid regions is larger than a predetermined variation reference. For example, the state determination part 240 calculates the distribution of the size of all spheroid regions, and determines whether or not the distribution is larger than the fourth threshold value. If the distribution of the size of the spheroids region is greater than or equal to the reference of the distribution, namely, if the distribution of the size of all the spheroid regions is equal to or greater than the fourth threshold value (Yes in the step S2400), the state determination part 240 proceeds to the step S2500. If the distribution of the size of the spheroid regions is smaller than the reference of the distribution, namely, if the distribution of the size of all spheroid regions is less than the fourth threshold value (No in the step S2400), the state determination part 240 proceeds to the step S1300.

Next, in the step S2500, the state determination part 240 determines that the culture state of the culture vessel containing the spheroid determined that the distribution of the size is large in the step S2400 is bad. In other words, the state determination part 240 determines that the culture state of the entire one culture vessel is bad. Furthermore, the state determination part 240 determines to discard all the spheroids of the culture vessel. In other words, the state determination part 240 determines the discard of the spheroids for each culture vessel. The state determination part 240 proceeds to the step S2700 after the processing of the step S2500.

The processing in the steps S1300 to S1600 is the same as that in the first embodiment. After the processing in the step S1600, the state determination part 240 proceeds to the step S2700.

In the step S2700, the display unit 150 displays the distribution of the size of the spheroids calculated in the step S2300 and determined in the step S2400 on the display. For example, the display unit 150 displays the size of the spheroid region calculated in the step S2300 as the size of the spheroid. Furthermore, the display unit 150 displays a histogram indicating the distribution of the size of the plurality of the spheroid regions as the distribution of the size of the spheroids. The display unit 150 may display a statistic amount such as the minimum value, the maximum value, the variance, and the standard deviation of the size of the plurality of the spheroid regions on the display. Further, the display unit 150 also displays the determination result of the step S1600. The display unit 150 may display simultaneously the display of the distribution of the size of the spheroids and the display of the determination result of the culture state, or may switch and display one of them. The display unit 150 may display the above information together with the display by an image, or separately from the display by the image, by outputting an audio signal.

For example, FIGS. 25A to 25D show examples of the display by the display unit 150. In this example, the display unit 150 is a display for displaying an image, and FIGS. 25A to 25D schematically show the examples of display screens on the display of the display unit 150.

Figure 25A:
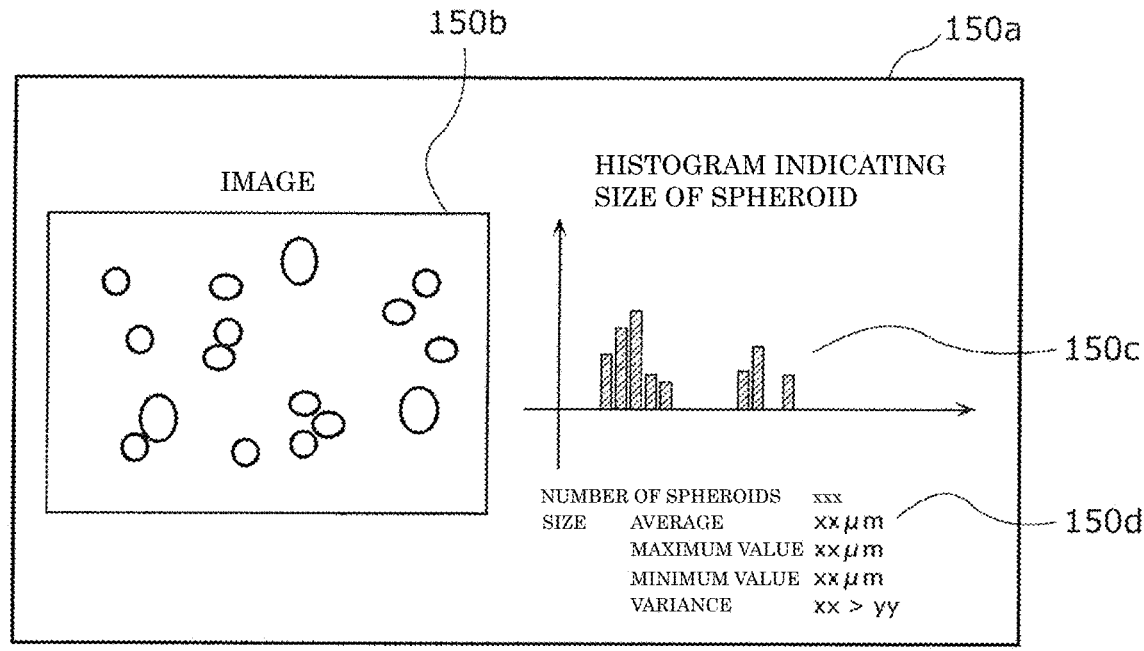
FIG. 25A is a diagram illustrating one example of display by a display unit according to the second embodiment.

FIG. 25A shows one state of a display screen 150a of the display unit 150. FIG. 25A shows a case where the culture state determination device 20 determines that the culture state of the spheroid is bad based on the distribution of the size of the spheroids. In the display screen 150a, an image 150b of the entire culture vessel is displayed in the left region. In the image 150b, the spheroids extracted as the spheroid regions in the step S2200 are displayed. Each spheroid is indicated by a line in which the outline of the spheroid region is emphasized, or by a circle or an ellipse surrounding the spheroid region. The image 150b is a selected one of the plurality of the captured images acquired in the step S1100, and may be a reference captured image.

For example, the reference captured image is an image captured during the illumination by the illuminator 101 located immediately above the center point of the image sensor 102.

In the upper right region of the display screen 150a, a histogram 150c indicating the distribution of the size of the spheroids calculated in the step S2300 is displayed. Further, in the display screen 150a, statistical information 150d on the spheroids is displayed in the lower right region. The statistical information 150d includes the number of the extracted spheroid regions, namely, the number of the spheroids and information on the size of the spheroids. In this example, the information on the size of the spheroids is the average, maximum value, minimum value, and variance of the size of the spheroids; however, is not limited thereto. Further, the statistical information 150d indicates the relationship between the variance and the fourth threshold value yy. In this example, it is indicated that the dispersion is larger than the fourth threshold value, namely, the dispersion is not less than the fourth threshold value. Thereby, the user who has seen the information 150d can recognize that the distribution of the size of the spheroids is large and that the spheroids are not suitable for the processing after the culture. In this case, the culture state determination device 20 determines that the distribution of the size of the spheroids is large in the step S2400, and does not perform the processing from the step S1300 to the step S1600. Therefore, since there is no information other than the information displayed in FIG. 25A, there is no display, on the display screen 150a, that presents calling of other information or switching of the display screen.

Figure 25B:
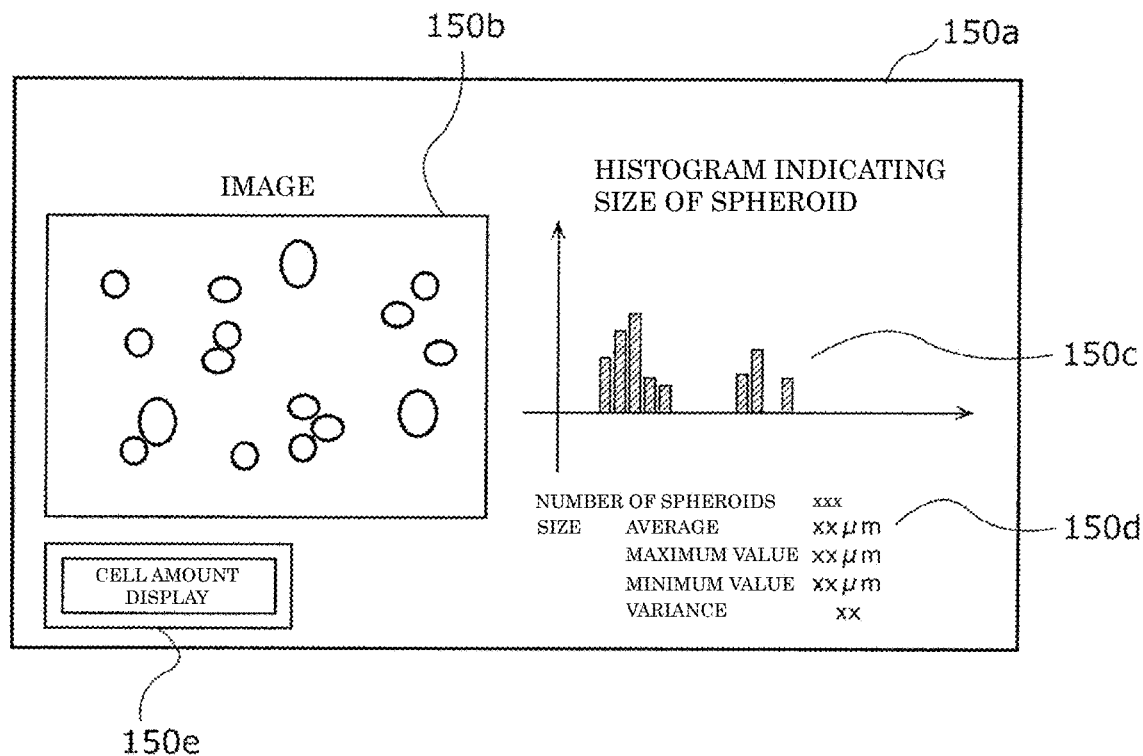
FIG. 25B is a diagram illustrating one example of display by the display unit according to the second embodiment.

FIG. 25B shows another state of the display screen 150a of the display unit 150. FIG. 25B shows a case where the culture state determination device 20 determines that the culture state of the spheroids is not bad based on the distribution of the size of the spheroids. In the display screen 150a, similarly to the case of FIG. 25A, the image 150b of the entire culture vessel, the histogram 150c showing the distribution of the size of the spheroids, and the statistical information 150d on the spheroids are displayed. In this case, a "cell amount display" icon 150e for displaying other information is displayed in the lower left region of the display screen 150a, namely, below the image 150b. Further, in the statistical information 150d, there is no display indicating that the distribution of the size of the spheroids is equal to or greater than the fourth threshold value. In this case, the culture state determination device 20 determines that the distribution of the size of the spheroids is within the reference in the step S2400, performs the refocusing processing through the processing from the step S1300 to the step S1600, and generates the in-focus image of each spheroid region. Then, the culture state determination device 20 calculates the first ratio between the total number of the first pixels in the outer shape of the spheroid and the total number of the second pixels in the cavity part of the spheroid.

Figure 25C:
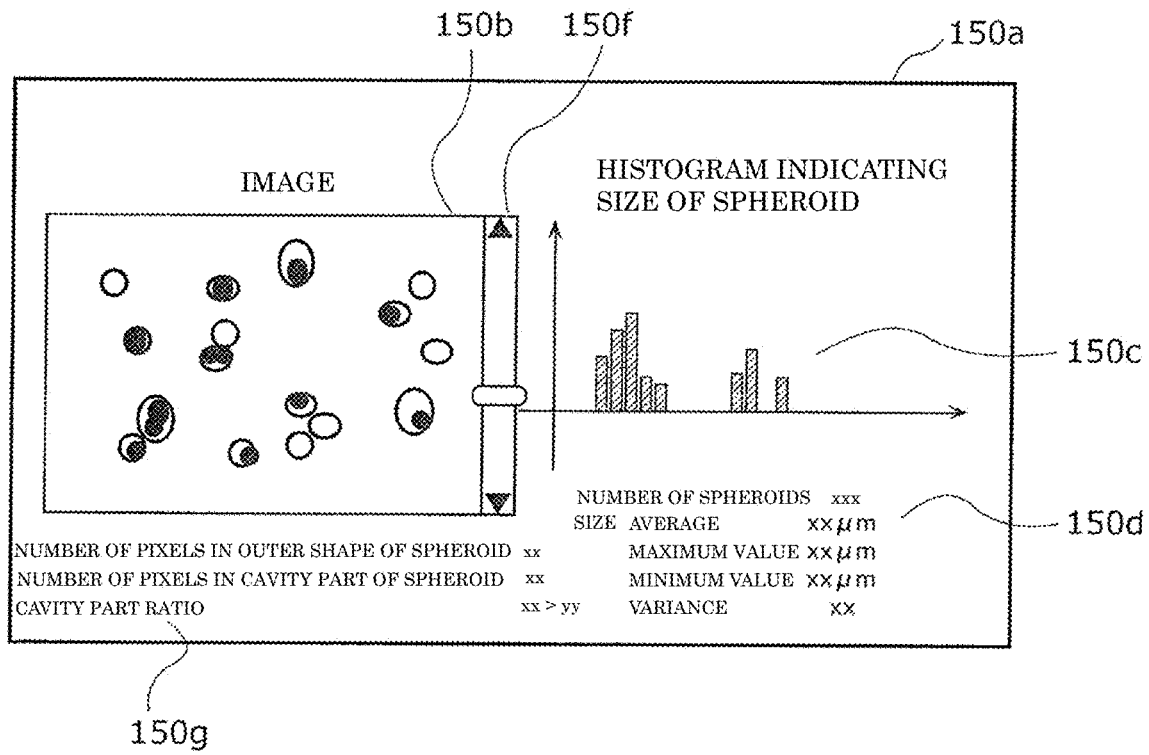
FIG. 25C is a diagram illustrating one example of display by the display unit according to the second embodiment.

FIG. 25C shows another state of FIG. 25B on the display screen 150a of the display unit 150. The display screen 150a in FIG. 25C is one example of a screen that is displayed after an input operation such as clicking on the "cell amount display" icon 150e in FIG. 25B. In the display screen 150a, similarly to the case of FIG. 25B, the image 150b of the entire culture vessel, the histogram 150c indicating the distribution of the size of the spheroids, and the statistical information 150d on the spheroids are displayed. Further, an input unit 150f for designating a focal plane to be displayed on the image 150b is displayed adjacent to the image 150b.

In this example, the input unit 150f is a slider. If the user moves the slider of the input unit 150f on the display screen 150a, the display unit 150 displays an in-focus image of each spheroid on the focal plane at a position corresponding to the position of the slider as the image 150b. In other words, the display unit 150 can display a cross-sectional image of each spheroid at an arbitrary focal plane. The moving direction of the slider corresponds to a direction toward and away from the light receiving surface of the image sensor 102, and the position of the slider corresponds to a distance from the light receiving surface of the image sensor 102.

Furthermore, information 150g on the cavity part of the spheroid is displayed in the lower left region of the display screen 150a, namely, below the image 150b. The information 150g includes the total number of the first pixels in the outer shape of the spheroid, the total number of the second pixels in the cavity part of the spheroid, and a cavity part ratio. The cavity part ratio is the first ratio. In this example, it is displayed that the cavity part ratio exceeds the determination reference value. As a result, the user who has seen the information 150g can recognize that the ratio of the cavity part of the spheroid is large, and the spheroid is not suitable for the processing after the culture.

Further, the input unit 150f may have any configuration other than the slider, as long as the focal plane can be selected through the input unit 150f. For example, the input unit 150f may be a key for receiving an input of a parameter such as a numerical value indicating the position of the focal plane, a touch panel for changing the focal plane to be displayed by receiving an input such as a slide on the image 150b, or a pointing device for selecting the focal plane.

Figure 25D:
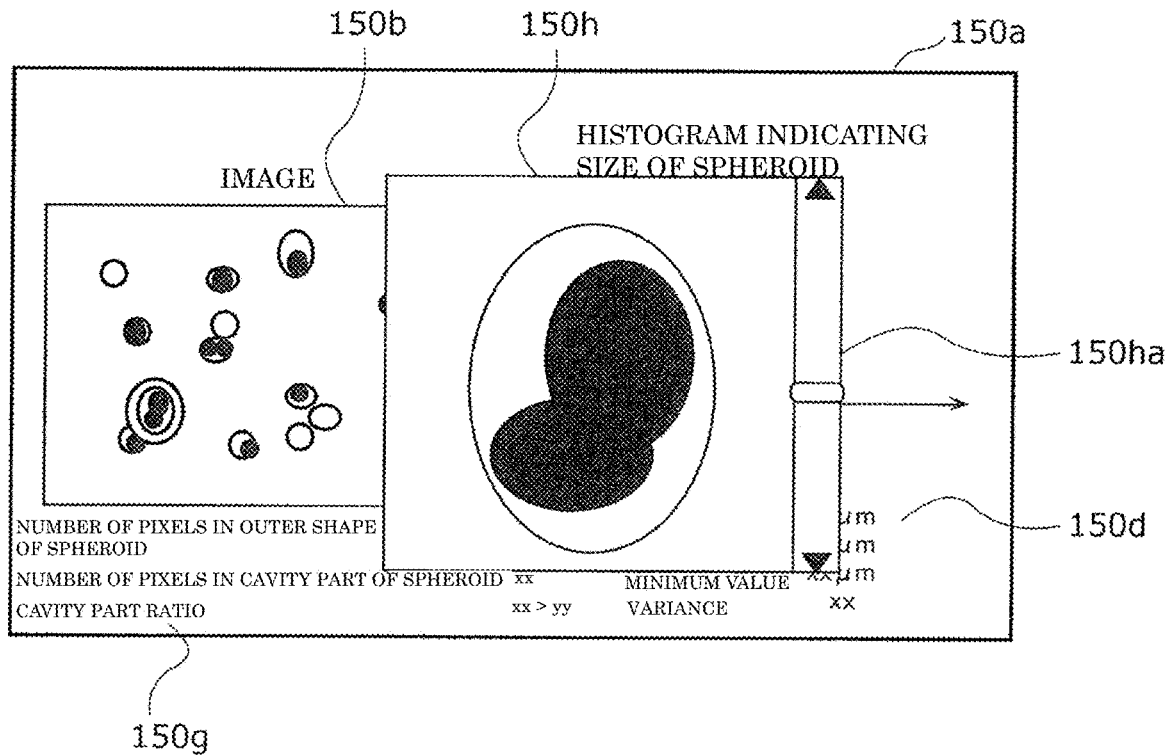
FIG. 25D is a diagram illustrating one example of display by the display unit according to the second embodiment.

FIG. 25D shows another state of FIG. 25C on the display screen 150a of the display unit 150. The display screen 150a in FIG. 25D is one example of a screen that displays an enlarged image 150h of a specific spheroid in a case where an image of the specific spheroid is designated on the display screen 150a in FIG. 25C. The designation of the image of the specific spheroid may be performed using a pointing device such as a cursor or a pointer in the display screen 150a. The enlarged image 150h may include an input unit 150ha for selecting a focal plane on which the in-focus image of the spheroid is displayed. The input unit 150ha may have the same configuration as the input unit 150f, and is a slider in this example. As a result, the user can display and visually recognize the arbitrary cross-sectional image of the selected spheroid on the enlarged image 150h.

In this way, the culture state determination device 20 uses the display screens 150a as shown in FIGS. 25A to 25D not only to display the determination results of the culture state for each culture vessel based on the distribution of the size of the spheroids and the amount of the cells in the spheroid but also to display a three-dimensional image of individual spheroids and provide a user with detailed information on the spheroids.

2-3. Effect

As described above, first, the culture state determination device 20 according to the second embodiment determines the distribution of the size of the plurality of the spheroids for the plurality of the spheroids cultured in the culture vessel. The culture state determination device 20 determines that all the spheroids in the culture vessel are discarded if the distribution is larger than the reference, and further determines the culture state if the distribution is smaller than the reference. As a result, when desired cells are acquired by the processing after the culture such as a differentiation processing, it is possible to easily select an efficient culture vessel. In the further determination of the culture state, with regard to the plurality of the spheroids in the culture vessel that have not been discarded due to the distribution, the culture state determination device 20 determines the quality of the culture state in the entire culture vessel based on the first ratio of the volume of the cavity part to the volume of the spheroid in the entire culture vessel, similarly to the case of the first embodiment.

The processing amount for calculating the first ratio with the refocusing processing is relatively large. On the other hand, the processing amount for determining the distribution of the size of the plurality of the spheroids in the culture vessel is significantly smaller than the processing amount for calculating the first ratio. The culture state determination device 20 improves processing speed for determining the culture state of the spheroids in the plurality of the culture vessels by decreasing the number of the culture vessels for which the first ratio is to be calculated based on the distribution of the size of the spheroids. As described above, the culture state determination device 20 determines the culture state of the spheroids during the culture for each culture vessel, and enables cultured cells in a state suitable for differentiation processing to be extracted efficiently.

Other Embodiments

Although the culture state determination device according to one or more aspects has been described based on the embodiments, the present disclosure is not limited to these embodiments. Various modifications conceived by those skilled in the art and forms constructed by combining components in different embodiments are also within the scope of the one or more aspects, unless deviating from the gist of the present disclosure.

The culture state determination device according to the embodiment calculates, for each spheroid, the number of the first pixels in the outer shape of the spheroid and the number of the second pixels in the cavity part of the spheroid on the in-focus image of each focal plane. Furthermore, the culture state determination device calculates the first total number by calculating the sum of the number of the first pixels at all the focal planes of all the spheroids, and calculates the second total number by calculating the sum of the number of the second pixels at all the focal planes of all the spheroids. However, the calculation method of the first total number and the second total number is not limited thereto. For example, for each spheroid, the culture state determination device may calculate the first total number by calculating the sum of the numbers of the first pixels at all focal planes and calculating the sum of the numbers of the first pixels of all the spheroids. Similarly, for each spheroid, the culture state determination device may calculate the second total number by calculating the sum of the numbers of the second pixels at all focal planes and calculating the sum of the numbers of the second pixels of all the spheroids. In this case, the culture state of each spheroid can be determined by calculating the volume of each spheroid and the volume of the cavity part of each spheroid.

Further, as described above, the technology of the present disclosure may be realized by a system, a device, a method, an integrated circuit, a computer program, or a recording medium such as a computer-readable recording disk. The the technology of the present disclosure may be realized by any combination of the system, the device, the method, the integrated circuit, and the computer program and the recording medium. The computer-readable recording medium includes a non-volatile recording medium such as a CD-ROM.

For example, each processing unit included in the culture state determination device according to the above embodiment is typically realized as a large scale integration (i.e., LSI) that is an integrated circuit. These may be individually made into one chip, or may be made into one chip so as to include a part or all of them.

Further, the circuit integration is not limited to LSI, and may be realized by a dedicated circuit or a general-purpose processor. A field programmable gate array (i.e., FPGA) that can be programmed after manufacturing the LSI, or a reconfigurable processor that can reconfigure the connection and setting of circuit cells inside the LSI may be used.

In the above embodiment, each component may be configured by dedicated hardware or may be realized by executing a software program suitable for each component. Each component may be realized by a program execution unit such as a processor such as a CPU reading and executing a software program recorded on a recording medium such as a hard disk or a semiconductor memory.

In addition, some or all of the above-described components may be configured from a removable integrated circuit (i.e., IC) card or a single module. The IC card or the module is a computer system that includes a microprocessor, ROM, and RAM. The IC card or the module may include the above-described LSI or a system LSI. The IC card or the module achieves its function by the microprocessor operating in accordance with the computer program. These IC cards and modules may have tamper resistance.

The culture state determination method of the present disclosure may be realized by a circuit such as a micro processing unit (i.e., MPU), a CPU, a processor, an LSI, an IC card, or a single module.

Furthermore, the technology of the present disclosure may be realized by a software program or a digital signal consisting of a software program, and may be a non-transitory computer-readable recording medium on which the program is recorded. In addition, the program can be distributed via a transmission medium such as the Internet.

In addition, all the numbers such as the ordinal numbers and the amounts used above are exemplified for specifically explaining the technology of the present disclosure, and the present disclosure is not limited to the illustrated numbers. In addition, the connection relationship between the constituent elements is exemplified for specifically explaining the technology of the present disclosure, and the connection relationship for realizing the functions of the present disclosure is not limited thereto.

In addition, division of functional blocks in the block diagram is one example. A plurality of functional blocks may be realized as one functional block. One functional block may be divided into a plurality of parts, or some functions may be transferred to other functional blocks. In addition, functions of a plurality of functional blocks having similar functions may be processed in parallel or time-division by a single hardware or software.

INDUSTRIAL APPLICABILITY

The technique of the present disclosure can be widely used for a technique for determining the culture state of stem cells such as tissue stem cells, iPS cells and ES cells in culture, or cell aggregations such as embryos. The technique of the present disclosure is useful for determining whether or not the culture state is suitable for differentiation processing when spheroids of pluripotent cells such as the stem cells are cultured and subjected to the differentiation processing.

REFERENCE SIGNS LIST 10, 20 Culture state determination device
100 Imaging device
101, 101a, 101b Illuminator(s)
102 Image sensor
103 Imaging control unit
110 Storage unit
120, 220 Image processing unit
121, 221 Region extraction unit
122 Internal image generation unit
123 Discrimination unit
130, 230 Calculation unit
140, 240 State determination unit
150 Display unit
1221 Refocusing Unit
1222 Focal plane table
1223 Image generation unit

The invention claimed is:

1. A culture state determination device, comprising:
a plurality of light sources;
an image sensor on which a plurality of cell aggregations are to be mounted; and
control circuitry which, in operation,
(a) repeatedly causes the image sensor to acquire an image of the plurality of cell aggregations when the plurality of cell aggregations are illuminated with each of the plurality of light sources sequentially, to acquire a plurality of images,
wherein each of the plurality of images includes an image of the plurality of cell aggregations,
(b) extracts an image region including an image of one cell aggregation from each of the plurality of images;
(c) generates three-dimensional image information with regard to the image region using the plurality of images;
(d) calculates a first volume and a second volume from the three-dimensional image information, wherein:
the first volume is an entire volume of the one cell aggregation, and
the second volume is a volume of a cavity part of the one cell aggregation;
(e) repeats the steps (b)-(d) to obtain first volumes of the plurality of cell aggregations, respectively, and second volumes of the plurality of ell aggregations, respectively;
(f) calculates a first total volume and a second total volume, wherein:
the first total volume is a sum of the first volumes of the plurality of cell aggregations, and
the second total volume is a sum of the second volumes of the plurality of cell aggregations; and
(g) determines a culture state of the plurality of cell aggregations using the first total volume and the second total volume, wherein:
the control circuitry determines whether or not distribution of size of regions of the plurality of cell aggregations is larger than a predetermined variation reference, after the step (b) and before the step (c), and
if the control circuitry determines that the distribution of the size of regions is larger than the predetermined variation reference, the control circuitry determines that the culture state of the plurality of cell aggregations is bad without performing the steps (c) to (f).

2. A method for determining a culture state, the method comprising:
(a) repeatedly causing an image sensor to acquire an image including a plurality of cell aggregations when the plurality of the cell aggregations are illuminated with each of a plurality of light sources sequentially, to acquire a plurality of images,
wherein each of the plurality of images includes an image of the plurality of cell aggregations;
(b) extracting an image region including an image of one cell aggregation from each of the plurality of images;
(c) generating three-dimensional image information with regard to the image region using the plurality of images;
(d) calculating a first volume and a second volume from the three-dimensional image information, wherein:
the first volume is an entire volume of the one cell aggregation, and
the second volume is a volume of a cavity part of the one cell aggregation;
(e) repeating the steps (b)-(d) to obtain first volumes of the plurality of cell aggregations, respectively, and second volumes of the plurality of ell aggregations, respectively;
(f) calculating a first total volume and a second total volume, wherein:
the first total volume is a sum of the first volumes of the plurality of cell aggregations, and
the second total volume is a sum of the second volumes of the plurality of cell aggregations;
(g) determining a culture state of the plurality of cell aggregations using the first total volume and the second total volume;
determining whether or not distribution of size of regions of the plurality of cell aggregations is larger than a predetermined variation reference, after the step (b) and before the step (c); and
after determining that the distribution of the size of regions is larger than the predetermined variation reference, determining that the culture state of the plurality of cell aggregations is bad without performing the steps (c) to (f).

3. A culture state determination device, comprising:
a plurality of light sources;
an image sensor on which a plurality of cell aggregations are to be mounted; and
control circuitry which, in operation,
(a) repeatedly causes the image sensor to acquire an image of the plurality of cell aggregations when the plurality of cell aggregations are illuminated with each of the plurality of light sources sequentially, to acquire a plurality of images,
wherein each of the plurality of images includes an image of the plurality of cell aggregations,
(b) extracts an image region including the image of the plurality of cell aggregations from each of the plurality of images;
(c) generates three-dimensional image information with regard to the image region using the plurality of images;
(d) calculates a first volume and a second volume from the three-dimensional image information, wherein:
the first volume is an entire volume of each of the plurality of cell aggregations, and
the second volume is a volume of a cavity part of each of the plurality of cell aggregations;
(e) calculates a first total volume and a second total volume, wherein:
the first total volume is a sum of first volumes with respect to the plurality of cell aggregations, and
the second total volume is a sum of second volumes with respect to the plurality of cell aggregations; and
(f) determines a culture state of the cell aggregation using the first total volume and the second total volume, wherein:
the control circuitry determines whether or not distribution of size of regions of the plurality of cell aggregations is larger than a predetermined variation reference, after the step (b) and before the step (c), and
if the control circuitry determines that the distribution of the size of regions is larger than the predetermined variation reference, the control circuitry determines that the culture state of the plurality of cell aggregations is bad without performing the steps (c) to (f).

4. A method for determining a culture state, the method comprising:
(a) repeatedly causing an image sensor to acquire an image of a plurality of cell aggregations when the plurality of cell aggregations are illuminated with each of a plurality of light sources sequentially, to acquire a plurality of captured images,
wherein each of the plurality of images includes an image of the plurality of cell aggregations,
(b) extracting an image region including the image of the cell aggregation from each of the plurality of images;
(c) generating three-dimensional image information with regard to the image region using the plurality of images;
(d) calculating a first volume and a second volume from the three-dimensional image information, wherein:
the first volume is an entire volume of each of the plurality of cell aggregations, and
the second volume is a volume of a cavity part of each of the plurality of cell aggregations;
(e) calculating a first total volume and a second total volume, wherein:
the first total volume is a sum of first volumes with respect to the plurality of cell aggregations, and
the second total volume is a sum of second volumes with respect to the plurality of cell aggregations;
(f) determining a culture state of the plurality of cell aggregations using the first total volume and the second total volume;
determining whether or not distribution of size of regions of the plurality of cell aggregations is larger than a predetermined variation reference, after the step (b) and before the step (c); and
after determining that the distribution of the size of regions is larger than the predetermined variation reference, determining that the culture state of the plurality of cell aggregations is bad without performing the steps (c) to (f).

* * * * *